(12) United States Patent
Jayson et al.

(10) Patent No.: US 7,919,599 B2
(45) Date of Patent: Apr. 5, 2011

(54) PRODUCTION OF L-IDURONATE CONTAINING POLYSACCHARIDES

(75) Inventors: Gordon Jayson, Manchester (GB); John Gardiner, Manchester (GB); Steen Hansen, Manchester (GB)

(73) Assignee: The University of Manchester (GB)

( * ) Notice: Subject to any disclaimer, the term of this patent is extended or adjusted under 35 U.S.C. 154(b) by 534 days.

(21) Appl. No.: 11/921,523

(22) PCT Filed: May 30, 2006

(86) PCT No.: PCT/GB2006/001965
§ 371 (c)(1),
(2), (4) Date: Nov. 30, 2007

(87) PCT Pub. No.: WO2006/129075
PCT Pub. Date: Dec. 7, 2006

(65) Prior Publication Data
US 2009/0137792 A1    May 28, 2009

(30) Foreign Application Priority Data

Jun. 3, 2005    (GB) .................................. 0511325.3

(51) Int. Cl.
*C07H 15/18* (2006.01)
*C07H 13/04* (2006.01)
*C07H 5/04* (2006.01)
*C07D 307/16* (2006.01)

(52) U.S. Cl. ....................................... 536/17.2; 549/435
(58) Field of Classification Search ........................ None
See application file for complete search history.

(56) References Cited

U.S. PATENT DOCUMENTS

| | | | |
|---|---|---|---|
| 5,399,201 | A | 3/1995 | Klingler et al. |
| 5,565,037 | A | 10/1996 | Sobotta et al. |
| 2002/0173632 | A1 | 11/2002 | Boldi et al. |

OTHER PUBLICATIONS

Davidson, "Conformation of the iduronic acid moiety of chondroitin sulfate B (Dermatan Sulfate)" Biochimica et Biophysica Acta (1965) vol. 1 No. 101, pp. 121-124.*
Buchynskyy et al., "Synthesis of tools for raising antibodies against moenomycin epitopes and initial immunological studies" Tetrahedron (2002) vol. 58 pp. 7741-7760.*
Barroca, et al., "Syntheses of b-D-Galp NAc4SO3-(1®4)-L-Idop A2SO3, a Disaccharide Fragment of Dermatan Sulfate, and of Its Methyl a-L-glycoside Derivative," Carbohydrate Research, vol. 329, No. 3, (2000), pp. 667-679.
Kovensky, et al., "Binding of Heparan Sulfateto Fibrolast Growth Factor-2 Total Synthesis of a Putative Pentasaccharide Binding Site," Tetrahedron Asummetry, vol. 7, No. 11, 1996, pp. 3119-3128.
Bazin, et al, "Regio and Stereoselective Converstion of D4-Uronic Acids to L-Ido- and D-Glucopyranosiduronic Acids," Tetrahedron Letters, vol. 38, No. 6, 1997, pp. 923-926.
Davis, et al., "Chemical Synthesis of Disaccharides which are Partial Structures of the Glycosaminoglycan Heparan Sulfate" Chem. Soc., vol. 1, No. 4, 1994, pp. 359-368.
Kiss, et al., "Synthesis of Heparin Saccharides, Part II1, Synthesis and Stereochemical Aspects of Anomeric Methyl (benzyl 2,3,-di-O-benzyl-L-idopyranoside) Uronates," Carbohydrate Research, vol. 27, 1973, pp. 282-285.
Kuszmann, et al., "Synthesis of 2,5-anhydro-(b-D-glycopyranosyluronate)- and (a-L-idopyranosyluronate)-D-mannitol Hexa-O-sulfonate hepta sodium salt,"Carbohydrate Research, vol. 339, 2004, pp. 1569-1579.
Poletti, et al., "A Rational Approach to Heparin-Related Fragments—Synthesis of Differently Sulfated Tetrasaccharides as Potential Ligands for Fibroblast Growth Factors," European Journal of Organic Chemistry, vol. 2001, No. 14, pp. 2727-2734.
Rauter, et al., "Synthesis of a-Methylene-g-Lactones in Furanosidic Systems," Journal of Carbohydrate Chemistry, vol. 6, No. 2, 1987, pp. 259-272.
International Search Report issued in connection with corresponding International Application No. PCT/GB2006/001965 on Sep. 29, 2006.
Great Britain Search Report issued in connection with corresponding Great Britain Application No. GB0511325.3 on Oct. 27, 2005.
Fernandez, et al., "Stereoselective Nucleophilic Formylation and Cyanation of a-Alkoxy- and a-Aminoaldehydes," Journal of Organic Chemistry, vol. 66, No. 15, 2001, pp. 5201-5207.
Rochepeau-Jobron, L.; Jacquinet, J-C. Carbohydr. Res. 1997, 303, 395-406.
Hinou, H.; Kuorsawa, H.; Matsuokak, K.; et al Tetrahedron Lett. 1999, 40, 1501-1504.
Schell, P.; Orgueira, H.A.; Roehrig, S., et al: Tetrahedron Lett. 2001, 42, 3811-3814.
Orgueira, H. A.; Bartolozzi, A.; Schell, P., et al Chem. Eur. J. 2003, 9, 140-169.
Ke, W.; Whitfield, D. M.; Gill, M.; et al., Tetrahedron Lett. 2003, 44, 7767-7770.
Ojeda, R.; de Paz, JL.; Martin-Lomas, M.; et al: Syn. Lett. 1999, 1316-1318.
Jacquinet, J-C.; Petitoi, M.; Duchaussoy, P.; et al Carbohydr. Res. 1984, 130, 221-241.
Lohman, G. J. S.; Hunt, D.K.; Hogermeier, J.A.; et al: J. Org. Chem., 2003, 68, 7559-7561.
Gavard, O.; Hersant, Y. I.; Alais, J.; et al., Eur. J. Org. Chem. 2003, 3603-3620.
Wolfrom, M. L.; Thomas, G. H. S , J., Carbohydr. Chem. 1987, 6, 259-272.. Methods in Carbohydr. Chem., Year/vol. 32-35.
Methods in Carbohydrate Chemistry. vol. II, p. 320-321 (2009).
Vogel's Textbook of Practical Organic Chemistry. 5th Edition. p. 656.

* cited by examiner

*Primary Examiner* — Eric S Olson
(74) *Attorney, Agent, or Firm* — Lerner, David, Littenberg, Krumholz & Mentlik, LLP

(57) ABSTRACT

The present invention provides processes for the production of polysaccharides containing the L-iduronate subunit, for example, heparin-type polysaccharides. New intermediate compounds and processes developed during the production of said polysaccharides are also presented.

80 Claims, No Drawings

PRODUCTION OF L-IDURONATE CONTAINING POLYSACCHARIDES

The present invention relates to the production of polysaccharides containing the L-iduronate subunit, particularly but not exclusively to heparin-type polysaccharides, and also to new intermediate compounds and processes developed during the production of said polysaccharides.

Carbohydrates represent one of the major classes of biomolecules and are critical to the regulation of a large number of biological processes and pathways. A common monosaccharide unit found in many carbohydrates is the L-Iduronate residue 1 (where, for example, R=SO$_3^-$) which is related to L-Iduronic acid 2.

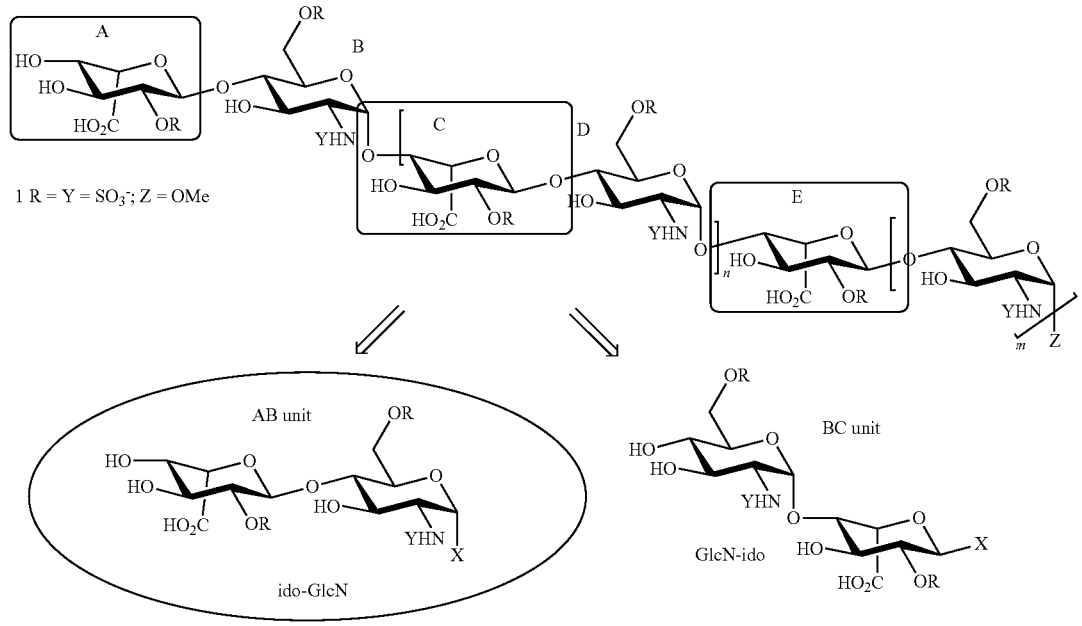

Examples of biologically important L-Iduronate-containing polysaccharides are heparan sulfate and heparin, which play a central role in many different biological processes including anti-coagulation, angiogenesis, cell growth and migration.

Heparan sulfate and heparin exist as complex heterogeneous mixtures of polysaccharide chains of varying length. The chains are principally composed of repeating disaccharide units as shown below in Schematic 1.

The repeating unit may be regarded as either an 'AB' glycosaminoglycan unit in which adjacent sugar rings are linked via a β(1→4)-glycosidic bond or a 'BC' glycosaminoglycan unit containing an α(1→4)-glycosidic bond. In each case, the disaccharide unit contains an L-iduronate moiety.

Medicinal drugs that promote or inhibit the function of heparan sulfate/heparin by mimicking or competitively inhibiting the function of heparan sulfate/heparin could potentially be used in a number of diseases that affect the general population. The therapeutic potential of these compounds includes cardiology/vascular medicine (anti-coagulation), cancer (angiogenesis and tumour growth), diabetic retinopathy (angiogenesis) and rheumatoid arthritis (angiogenesis in the pannus). By way of example, heparan sulfate and heparin are known to be involved in the regulation of the fibroblast growth factor FGF-2. In view of the fact that FGF-2 has been implicated in angiogenesis, FGF-2 inhibitory heparin systems have great potential as anti-angiogenic/anti-tumour agents. More recently, pathological studies in Alzheimer's disease have suggested that heparan sulfate may be pathophysiologically relevant and there is therefore a further potential market for saccharide based drugs in that setting. Commercial production of drugs that promote or inhibit the function of heparan sulfate and/or heparin will therefore be reliant on the development of viable syntheses of L-iduronic acid and its derivatives.

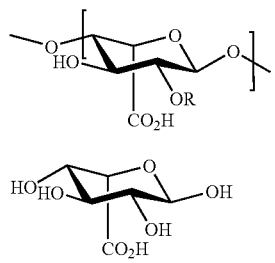

L-Iduronic acid is a 'rare' sugar in that it possesses the L-configuration at the C5 position whereas all other common, readily available sugars possess the opposite D-configuration at C5. As a result, commercially viable syntheses of L-Iduronic acid, its derivatives and polysaccharides containing L-Iduronate subunits from readily available sugars have not yet been developed. Synthesis of L-Iduronic acid and its derivatives is therefore of significant commercial importance since these compounds are not available at viable cost from natural sources.

The importance of L-iduronic acid has led to the development of a number of different approaches to synthesising this molecule. However, all current synthetic routes employ expensive reagents under conditions that would be difficult to scale up. One of the principal synthetic difficulties is the generation of the correct stereochemistry at the C5 position of the molecule.

Several earlier methods start from the more available D-sugar precursors and invert the C5 stereochemistry from the D-configuration to the L-configuration. For example, conversion of glucose stereochemistry via formation and then reduction of exo-glucals has been used with mono-glucosides[1] and trehalose (α,α-linked diglucoside)[2]. Base-mediated epimerization of a D-configuration carboxylate ester glycal has also been reported.[3] These approaches are not commercially viable because they generate diastereoisomeric mixtures and are significantly limited in scalability.

The most recent syntheses originate from the groups of Seeberger[4], Whitfield[5] and Martin-Lomas[6] who have reported routes which involve overall inversion of the C5 configuration of D-gluco precursors. Whitfield[5] and Martin-Lomas[6] start with D-glucoronolactone and use triflate inversion chemistry but the overall routes use several steps with low temperatures (i.e. −30° C.). The Whitfield route[5] additionally requires synthesis of a tertiary-butyldimethylsilyl (TBDMS) glycosidic ether intermediate, which is not viable on a large scale due to the very high molar cost of TBDMS reagents. Seeberger's route[4] involves known elaborations involving a very similar C5 inversion, again via a C5 triflate, but moving the inversion step to after the lactone cleavage step. The Seeberger route (disclosed in International Patent publication no. WO 02/058633) proceeds through the same known intermediate as the Whitfield[5] and Martin-Lomas[6] routes and is also very comparable to Sinay's approach of 1984.[7] The Seeberger[4], Whitfield[5] and Martin-Lomas[6] routes all require 8 to 12 steps to provide the basic L-iduronic acid unit even before any manipulation to enable differentiation of O1, O2 or O4. These routes are therefore unlikely to offer commercially viable scalable syntheses.

The groups of Seeberger[8] and Bonaffe[9] have more recently reported alternative approaches to those described above. Each of these methods employs the same basic chemistry and involves the addition of a trithiane unit to the known aldehyde 3 (3-O-benzyl-1,2-O-isopropylidene-α-D-xylo-dialdose) at very low temperature and under inert conditions to control the diastereoselectivity of the addition step.

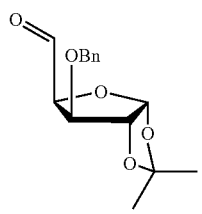

3

However, trithiane is very expensive and the need for low temperatures and very inert conditions at this key step (and others) is likely to make the Seeberger and Bonaffe methods difficult to scale up. Moreover, addition of nucleophiles to the aldehyde 3 are known to show variable stereoselectivity, for example nucleophilic addition of cyanide to aldehyde 3 has yielded very poor L-Ido/D-gluco diastereocontrol[10], which indicates that this is not a viable strategy for obtaining products with the required stereochemistry.

The object of the present invention is to obviate or mitigate one or more of the above problems.

According to a first aspect of the present invention there is provided a process for converting α-D-glucose 4 to oα-L-idofuranonitrile 5' via α-D-xylo-dialdose 3'

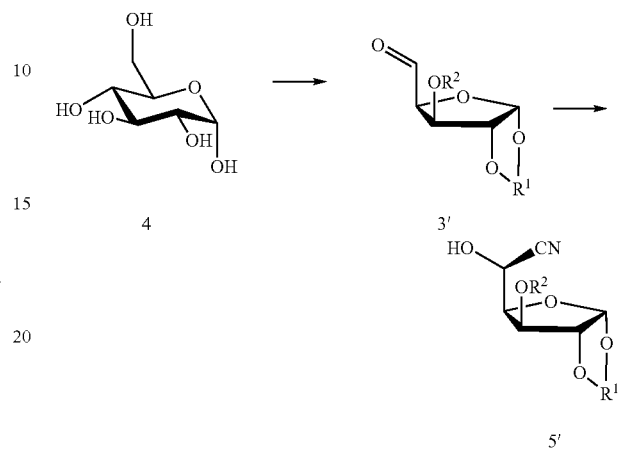

where $R^1$ is an alkylene group and $R^2$ is a protecting group, wherein the conversion of compound 3' to compound 5' is effected by reacting compound 3' with cyanide ions in the presence of magnesium ions.

The present invention therefore provides a process for effecting the conversion of α-D-glucose 4 to α-L-idofuranonitrile 5', as shown below

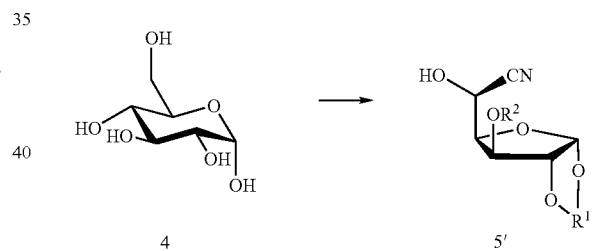

This process represents a commercially viable method to effect the above conversion of the cheap readily available sugar, α-D-glucose 4 to the product 5', which has the desired L-configuration at the C5 carbon atom to facilitate subsequent conversion of the compound 5' to stereopure L-iduronic acid and derivatives thereof. This represents an important step towards producing L-iduronate-containing disaccharide units, such as those found in heparan sulfate and heparin, which can ultimately be used in the production of synthetic L-iduronate-containing oligosaccharides and polysaccharides. Moreover, the fact that the conversion of compound 4 to compound 5' may be carried out at room temperature in air and without exclusion of moisture makes this method particularly suitable for industrial application.

The conversion of α-D-glucose 4 to the idofuranonitrile product 5 may be carried out conventionally.

While it is most desirable to effect conversion of compound 3' to a single stereochemically pure product 5', the reaction of compound 3' with cyanide ions typically generates a product mixture of compounds 5' and 6' as shown below, where compound 6' is an α-D-glucofuranonitrile.

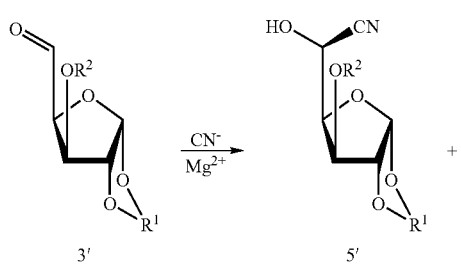

The desired product, compound 5', can be isolated from the product mixture by redissolving the crude product in an aprotic organic solvent, such as diethylether or ethylacetate, and then adding a non-polar solvent, such as hexane to induce compound 5' to crystallise out, and the remaining product mixture then re-equilibrated by adding cyanide ions in the presence of magnesium ions to provide a further product mixture containing additional compound 5' and compound 6', and isolating a further amount of compound 5' from said further product mixture.

It is possible to optimise the various reagents and reaction parameters to provide highly stereoselective conversion of compound 3' to compound 5', i.e. to provide a relatively high product ratio of 5':6'. The reaction is preferably carried out under stereoselective conditions to provide a product ratio of 5':6' of greater than 2:1, more preferably greater than 5:1, yet more preferably greater than 10:1, and most preferably greater than 15:1.

It is generally preferred that the molar ratio of magnesium ions to cyanide ions is greater than or equal to 0.5 (i.e. at least twice the molar amount of cyanide ions compared to magnesium ions is used). More preferably the molar ratio of magnesium ions to cyanide ions is in the range 0.5 to 2, still more preferably in the range 0.8 to 1.2, and most preferably an approximately equal molar amount of magnesium ions and cyanide ions (i.e. an $Mg^{2+}$:$CN^-$ molar ratio of around 1:1) is used.

Preferred sources of cyanide ions include potassium cyanide, sodium cyanide, hydrogen cyanide and lithium cyanide. It will be evident to the skilled person that to effect the above conversion at least approximately 1 molar equivalent of cyanide ions compared to the amount of compound 3' should be used. For example, a small excess of cyanide ions (e.g. an amount of around 1.1 equivalents by mole) may be provided based on the amount of compound 3'.

Any desirable source of the magnesium ions may be used, although it is preferred that the magnesium ion source is selected from the group consisting of magnesium halide and magnesium sulphate. The most preferred source of magnesium ions is magnesium chloride.

The reaction to convert compound 3' to compound 5' is preferably conducted at a temperature in the range 0° C. to 40° C., more preferably 10° C. to 30° C. and still more preferably 15° C. to 25° C. It is most preferred that a reaction temperature of around room temperature is used.

A wide range of reaction times may be used depending upon the various other reaction parameters and the ratio of products (i.e. 5':6') which is required. Preferably compound 3' is converted to compound 5' employing a reaction time of 1 hour to 10 days. More preferably a reaction time of 1 to 6 days is used and yet more preferably a reaction time of 2 to 5 days is used.

While the reaction to produce compound 5' from compound 3' may be conducted in any appropriate solvent, the reaction is preferably carried out in an alcoholic solvent, which is preferably an aqueous alcoholic solvent. The alcohol may be an alkanol, preferably a $C_1$ to $C_3$ alkanol, and is most preferably ethanol. Where the reaction solvent is an aqueous alcoholic solvent, the ratio of alcohol to water is preferably in the range 3:1 to 1:3. For example, the alcohol to water ratio may be in the range 2:1 to 1:2, more preferably in the range 0.8:1 to 1:0.8, and a most preferred alcohol to water ratio is around 1:1.

The $R^1$ alkylene group bonded to the C1 and C2 oxygen atoms acts as a protecting group. It is preferred that $R^1$ provides at least one carbon atom between the C1 and C2 oxygen atoms, i.e. $R^1$ is preferably at least a $C_1$ alkylene group. For example, $R^1$ may be a methylene group or an isopropyl group.

$R^2$ is preferably a benzyl group but may be any appropriate protecting group such as a substituted or unsubstituted acyl group, e.g. an acetyl group.

Therefore a preferred compound of general formula 3' is 3-O-benzyl-1,2-O-isopropylidene-α-D-xylo-dialdose 3 as shown below.

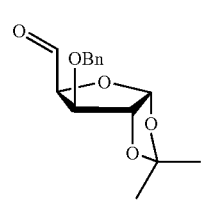

Furthermore, a preferred compound of general formula 5' is 3-O-benzyl-1,2-O-isopropylidene-α-L-idofuranonitrile 5 as shown below.

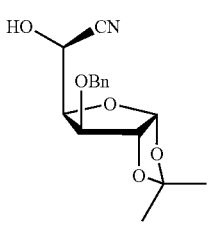

Preferred compound 3 may be produced from α-D-glucose 4 by conversion to diacetone-D-glucose using known methods, i.e. 3-O-benzylation, selective removal of the 5,6-isopropylidene and then oxidation with potassium periodate or sodium periodate.

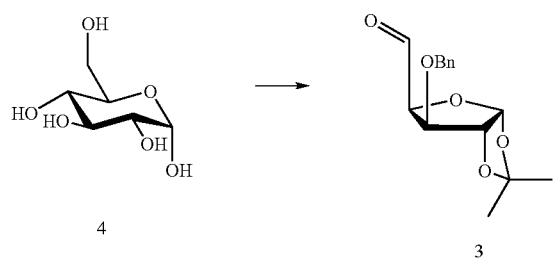

Preferred compound 5 may then be prepared by reacting compound 3 with cyanide ions in the presence of magnesium ions.

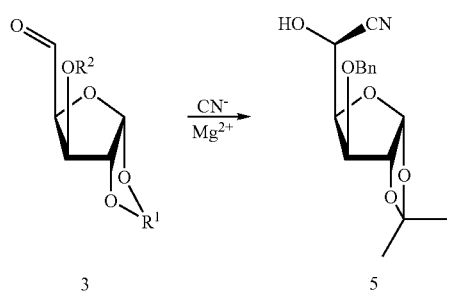

The best combination of product stereoselectivity and reaction yield for the above conversion of compound 3 to compound 5 may be obtained by reacting compound 3 with 1.1 molar equivalents of cyanide ions (from KCN) in the presence of 1.1 molar equivalents of magnesium ions (from $MgCl_2$) (molar equivalents based on the amount of compound 3) in an ethanol/water (1:1) solvent at room temperature over a period of 5 days. This method produces an overall yield of 76% of a product mixture containing preferred compound 5 and the related compound 6 (3-O-benzyl-1,2-O-isopropylidene-α-D-glucofuranonitrile) in a product ratio (5:6) of 20:1.

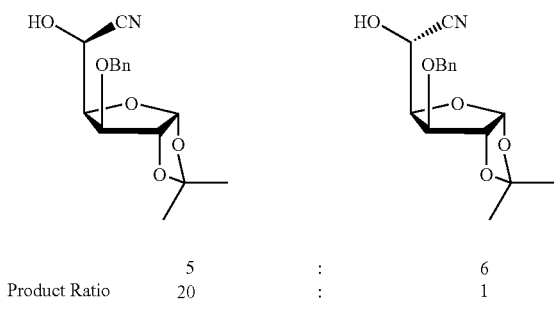

It has been observed that the presence of magnesium ions plays a role in controlling the stereochemical ratio (5':6') of the products obtained by reacting compound 3' with cyanide ions. A series of comparative experiments was carried out using preferred compound 3 to investigate how the product ratio varied in the presence of different salts and different molar equivalent amounts of magnesium chloride (see Comparative Example 1). The results of these experiments illustrate that an excess of the desired product 5 is achieved by carrying out the cyanohydrin reaction in the presence of at least approximately 0.5 molar equivalents of magnesium ions. Carrying out the reaction in the presence of calcium ions or using only a very small amount (0.1 molar equivalents) of magnesium ions did not yield the desired product ratio. Additionally, the total product yield was notably lower when calcium chloride or just a small amount of magnesium chloride was used.

The results presented in Comparative Example 1 also demonstrate that satisfactory product ratios can be obtained using a cheap and readily available solvent (ethanol/water) and carrying out the reactions at room temperature. Both of these factors represent significant improvements to prior art methods and further facilitate commercial application of the inventive process.

Further comparative experiments were carried out to investigate the product ratio obtained by varying the amount of magnesium chloride, solvent, temperature and time period over which the cyanohydrin reaction was carried out (see Comparative Example 2). The results of these experiments showed that the highest product ratios (5:6) were obtained by using a slight molar excess of magnesium chloride and potassium cyanide compared to the amount of aldehyde 3, conducting the experiments at room temperature and using a 1:1 ethanol/water solvent. The three reactions employing these reagents and conditions are the top three entries in Table 2 where it can be seen that each reaction provided a product ratio (5:6) of at least 3:1, with the best combination of total yield (76%) and product ratio (20:1) being obtained using a reaction time of 5 days.

The fourth and fifth results shown in Table 2 illustrate that an excess of compound 5 compared to compound 6 can be obtained by conducting the reaction in a solvent having a higher proportion of ethanol over a shorter period of time compared to the above preferred method. For example, the fourth result in Table 2 demonstrates that an acceptable product ratio of 2:1 can be achieved by reacting aldehyde 3 with 1.1 molar equivalents of cyanide ions in the presence of 1.1 molar equivalents of magnesium chloride in a 2:1 ethanol/water solvent at room temperature over a period of 16 hours.

Further comparative experiments were carried out to investigate the product ratio and diastereoisomeric excess (d.e.) obtained by varying the reaction time and the starting concentration of aldehyde 3 (see Comparative Example 3). The results of these experiments are provided in Table 3 and illustrate that the highest d.e. was obtained by employing an aldehyde 3 concentration of 0.3 M and carrying out the reaction over a period of 5 days, which further supports the above definition of a most preferred method for effecting the conversion of the aldehyde 3 to compound 5.

Conversion of aldehyde 3 to compound 5 with a high d.e. with respect to compound 6 was also obtained by employing the same reaction conditions as the most preferred method but using a shorter reaction time. As can be seen from Table 3, compound 3 may be converted to compound 5 employing a reaction time of at least 20 minutes, however, when a reaction time of at least 2 hours was used the d.e. improved significantly. When a reaction time of 48 hours was used the d.e. was almost as high as when the most preferred reaction time of 5 days was used. Thus, a reaction time of around 48 hours may be suitable for certain industrial applications given that shorter reaction times can improve production efficiency.

The three results obtained when using different concentrations of aldehyde 3 (see the bottom three results in Table 3) indicate that an acceptable d.e. (i.e. a product mixture containing predominantly compound 5) can be obtained for a wide range of aldehyde 3 concentrations, but that it is preferred that an aldehyde 3 concentration of greater than 0.06 M is used. Very high d.e.s of 75% or more can be obtained using an aldehyde concentration of at least 0.19 M. The results presented in Table 3 also demonstrate that if it is desirable to use a reaction time of around 16 hours then it is preferred that an aldehyde 3 concentration of at least 0.19 M is used, more preferably a concentration of at least 0.3 M and most preferably an aldehyde 3 concentration of approximately 0.55 M is used.

In the case where preferred reagents and reaction parameters produce lower product ratios, for example where is it preferable to use the shortest possible reaction time, as described above the desired product, compound 5', can be first isolated from the product mixture and the remaining product mixture then re-equilibrated by adding cyanide ions in the presence of magnesium ions to provide a further product mixture containing additional compound 5', and isolating a further amount of compound 5'.

For the case where a product ratio (5:6) of 2:1 has been obtained (see entries 2 and 10 in Table 3) compound 5 may be crystallised out to provide pure 5 and the remaining product mixture then re-equilibrated by adding a small amount of cyanide ions and magnesium ions (e.g. 0.1 molar equivalents of KCN and $MgCl_2$). This re-equilibrated mixture may contain compounds 5 and 6 in a relatively high product ratio (5:6) of, for example, 20:1, which can then be processed as described above to isolate compound 5.

Thus, partly selective mixtures of compounds 5' and 6' may be a source of pure compound 5 by employing an appropriate crystallization methodology and any relatively unselective mixtures of compounds 5' and 6' may be re-equilibrated under suitable conditions to provide a more highly selective product mixture which significantly increases the efficiency of the process and makes it eminently suitable for industrial application.

Having established a commercially viable process for the production of the α-L-idofuranonitriles 5 and 5', a further aspect of the present invention relates to effecting the conversion of compound 5' to a compound having the formula 7 as shown below

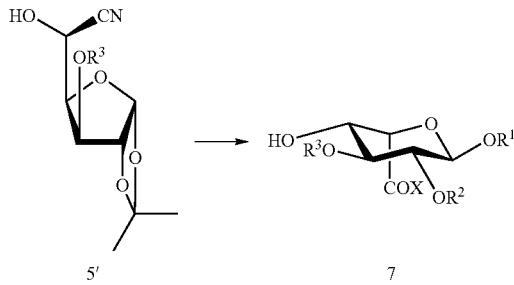

where $R^1$, $R^2$ and $R^3$ are the same or different protecting groups and X is selected from the group consisting of —$NH_2$, —OH and —OR, wherein the process comprises converting the C5 cyano group of compound 5' to the —COX group of compound 7, deprotecting the C1 and C2 oxygen atoms and then adding protecting groups $R^1$ and $R^2$ to the C1 and C2 oxygen atoms.

A preferred compound of general formula 5' is compound 5 and so this aspect of the invention provides a process to effect the following conversion.

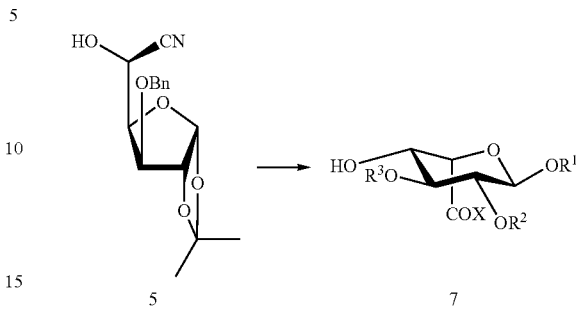

where $R^1$, $R^2$ and $R^3$ are the same or different protecting groups and $R^1$ and $R^2$ may be linked (e.g. by both $R^1$ and $R^2$ forming part of a cyclic acetal group), and X is selected from the group consisting of —$NH_2$, —OH and —OR to provide respectively amide, carboxylic acid or ester functional groups at the C5 position.

Another related aspect of the present invention provides a compound having the formula 7'

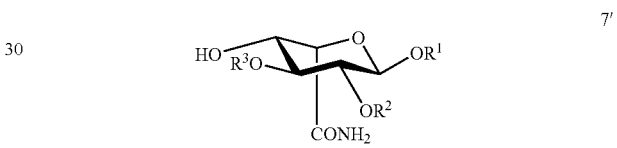

where $R^1$, $R^2$ and $R^3$ are the same or different protecting groups.

A preferred compound of general formula 7 is 1,2-di-O-acetyl-3-O-benzyl-β-L-idopyranuronamide 8.

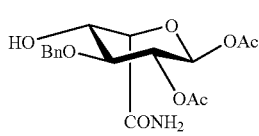

The β-L-idopyranuronamide 8 can be produced from the α-L-idofuranonitrile 5 via formation of a mixture of 5- and 6-membered ring compounds 9 and 10 as shown below.

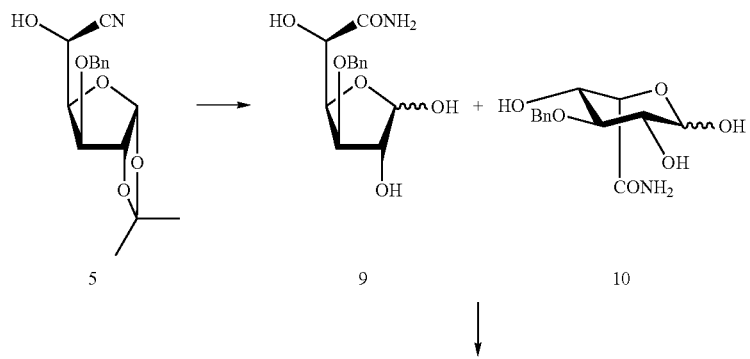

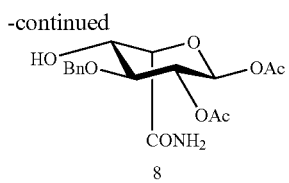

8

The above conversion of compound 5 to the mixture of compounds 9 and 10 involves deprotection of the C1 and C2 oxygen atoms. Acid catalysed deprotection yields C1 and C2 hydroxyl groups and results in generation of both the α- and β-anomers of compounds 9 and 10. The deprotection step is preferably effected by the addition of a suitable aqueous acid, such as aqueous hydrochloric acid. A particularly preferred aqueous acid is an aqueous solution containing 30% hydrochloric acid. Preferably the conversion is carried out at room temperature.

Compound 8 can be formed by selectively acetylating just the C1 and C2 hydroxyl groups of compounds 9 and 10. It is not necessary to isolate either compound 9 or 10 from the product mixture obtained by the deprotection of compound 5 in order to prepare compound 8. The mixture may simply be prepared as described above and then subjected to the appropriate conditions to effect acetylation at the C1 and C2 positions such that both 9 and 10 are converted to 8.

Acetylation may be achieved by adding an acetylating agent, such as acetic anhydride or an acetyl halide under suitable conditions. It has been found that a preferred method for effecting the selective acetylation is to add acetic anhydride and dimethylaminopyridine (DMAP) to the mixture of compounds 9 and 10, most preferably in dichloromethane or THF. The desired product, compound 8, may then be isolated after a reaction time of approximately 4 to 8 hours, or more preferably, after a reaction time of approximately 6 hours.

Isolation of compound 8 may be effected by initially washing the product of the acetylation reaction with a base (for example, a weak base such as sodium hydrogencarbonate), adding an appropriate amount of acid (e.g. a weak aqueous acid, such as an aqueous solution of 1% hydrochloric acid) followed by drying and evaporation of any residual solvent. Preferably, the crude product is purified by crystallisation, which may be effected by redissolving the crude product in an aprotic organic solvent (e.g. diethylether or ethylacetate) and then adding a non-polar solvent, such as hexane. If desired, further purification may be achieved by one or more rounds of recrystallisation. In order to improve the overall efficiency of the conversion of compounds 9 and 10 to compound 8, any partially acetylated residues which did not fully precipitate out upon addition of the non-polar solvent may be deacetylated back to compound 10 by dissolving in methanol and adding a catalytic amount of sodium.

If all of the hydroxyl groups of compounds 9 and 10 are protected then an alternative to compound 8 is produced, compound 11'. The production of compound 11' from compound 5' as shown below represents another aspect of the invention.

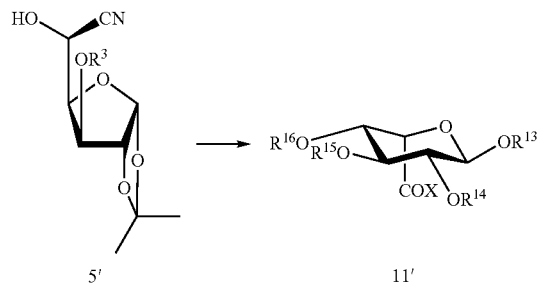

where $R^3$, $R^{13}$, $R^{14}$, $R^{15}$ and $R^{16}$ are the same or different protecting groups and X is selected from the group consisting of —$NH_2$, —OH and —OR, wherein the process comprises converting the C5 cyano group of compound 5' to the —COX group of compound 11', deprotecting the C1 and C2 oxygen atoms and then adding protecting groups $R^{13}$, $R^{14}$ and $R^{16}$ to the C1, C2 and C4 oxygen atoms respectively.

If all of the hydroxyl groups of compounds 9 and 10 are completely acetylated then an alternative compound is produced, 1,2,4-tri-O-acetyl-3-O-benzyl-β-L-idopyranuronamide 11, which represents a preferred compound of general formula 11'.

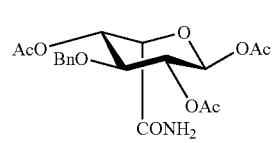

11

Complete acetylation may be achieved by adding an acetylating agent, such as acetic anhydride or an acetyl halide under suitable conditions. It has been found that a preferred method for effecting complete acetylation is to add acetic anhydride. If the acetylation is carried out starting from compound 10 alone, then it is preferred that compound 10 is reacted with acetic anhydride in the presence of pyridine using dichloromethane as solvent. The desired product, compound 11, may then be isolated after a reaction time of approximately 1 to 2 hours, or more preferably, after a reaction time of approximately 1.5 hours. Compound 11 may be isolated by evaporating any solvent present, followed by column chromatography employing a suitable eluent, such as 1:1 ethylacetate/hexane, or by crystallization most preferably from ethyl acetate/hexane mixtures.

It is preferred that the above conversions of compound 5' to the β-L-idopyranuronamides 8 and 11 via the mixture of compounds 9 and 10 are effected under ambient conditions. The realisation that compounds 8 and 11 may be prepared from compound 5' under non-inert conditions together with the fact that the conversions can be carried out at room temperature using cheap and readily available reagents and solvents makes each of these processes eminently suitable for industrial application. These processes therefore provide commercially viable methods for producing compounds 8 and 11 which can be subsequently converted, as described below, into glycosyl donor or acceptor compounds for coupling to appropriate monosaccharide residues to produce L-iduronate containing disaccharides and polysaccharides.

A further compound of general formula 7 which can be prepared from compound 5' and may be converted into a glycosyl donor or acceptor compound for use in the production of L-iduronate containing disaccharides and polysaccharides is compound 12' as shown below

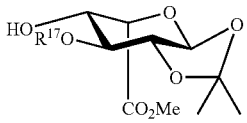

where $R^{17}$ is a protecting group, such as substituted or unsubstituted acyl protecting group, a substituted or unsubstituted carbocyclic protecting group or a substituted or unsubstituted heterocyclic protecting group. Particularly preferred protecting groups are acetyl groups, a benzyl groups and a tetrahydropyranyl groups.

A preferred example of a compound of general formula 12' is methyl 3-O-benzyl-1,2-O-isopropylidene-β-L-idopyranosyluronate 12.

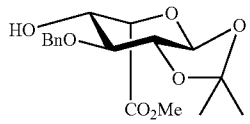

may, for example, be achieved by first oxidising the cyano group to an amide group and then converting the amide group to the ester group.

Preferred examples of compounds 5' and 12' are methyl 3-O-benzyl-1,2-O-isopropylidene-β-L-idopyranosyluronate 12 and 3-O-benzyl-1,2-O-isopropylidene-α-L-idofuranonitrile 5 respectively. A preferred embodiment of this aspect of the invention is therefore the conversion of compound 5 to compound 12 as shown below.

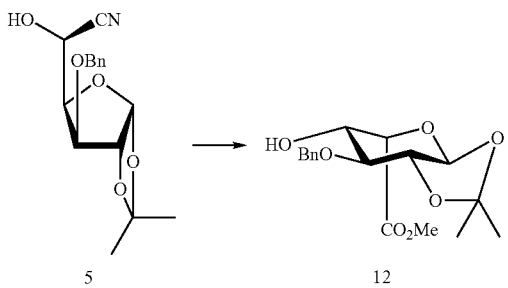

A preferred sequence of steps to effect the above conversion is shown below.

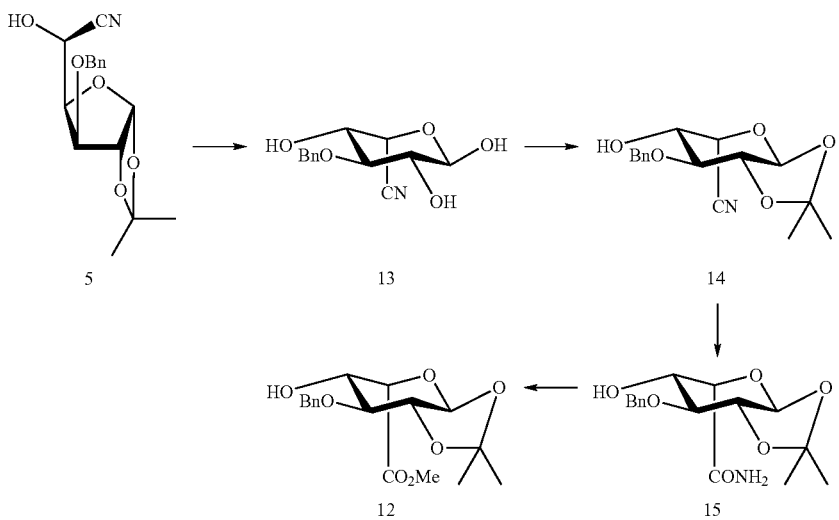

A further aspect of the present invention relates to the production of compound 12' from compound 5', thus

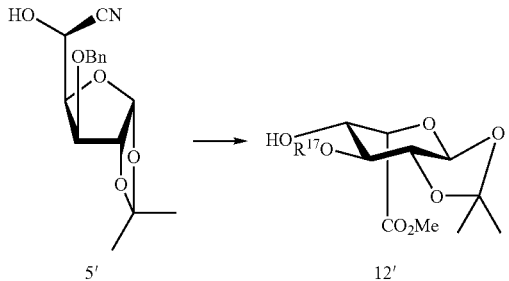

A preferred method for producing compound 12' from compound 5' comprises deprotecting the C1 and C2 oxygen atoms of compound 5' to allow the 5-membered furanose ring structure to convert to the corresponding 6-membered pyranose ring structure, reprotecting the C1 and C2 oxygen atoms, and converting the C5 cyano group to an ester group, which Deprotection of the C1 and C2 oxygen atoms of compound 5 is preferably effected using a strong acid, such as trifluoroacetic acid (TFA). Water may be added after addition of the TFA. A reaction time of 15 to 45 minutes may be employed, or more preferably, a reaction time of approximately 30 minutes is used. After an appropriate reaction time, the solvent(s) are preferably removed in vacuo and, most preferably, further water added and subsequently removed in vacuo. Conveniently, the residue may be dissolved (e.g. in ethylacetate), filtered and compound 13 crystallised from hexane.

A further aspect of the present invention provides the new compound 3-O-benzyl-1,2-O-isopropylidene-β-L-idopyranonitrile 14. It is preferred that compound 5 is first converted to compound 13 as described above prior to conversion to compound 14. Production of the β-L-idopyranonitrile 14 from compound 13 is preferably effected by the addition of 2-methoxy-propene in the presence of a catalytic amount of camphorsulfonic acid (e.g. less than 0.05 equivalents, more preferably approximately 0.02 equivalents and most preferably around 0.004 equivalents, by mole of camphorsulfonic acid compared to the amount of 2-methoxy-propene) followed by replacement of the resulting C4 2-methoxy-isopropyl ether group with a hydroxyl group by adding p-toluenesulfonic acid mono hydrate. It is preferred that less than 0.5 equivalents, more preferably approximately 0.1 equivalents, by mole of p-toluenesulfonic acid mono hydrate is used. Reaction of the 2-methoxy-propene with compound 13 may be effected over a time period of up to 48 hours but is more preferably effected over approximately 36 hours, after which the reaction may be quenched by the addition of a suitable quenching agent, such as triethylamine, and any residual solvent removed. The product of this initial reaction, 3-O-benzyl-1,2-O-isopropylidene-4-O-(2-methoxy-isopropyl)-β-L-idopyranonitrile, i.e. compound 14 with a C4 2-methoxy-isopropyl group instead of the C4 hydroxyl group, may then be converted to compound 14 by adding p-toluenesulfonic acid mono hydrate as described above and then quenching the reaction after a suitable period of time (e.g. up to 24 hours, more preferably around 18 hours) by adding a quenching agent. As before, a suitable quenching agent is triethylamine. Following subsequent removal of the solvents, the β-L-idopyranonitrile product 14 may be obtained by column chromatography. A suitable eluent is 1:3 ethylacetate/hexane. This chromatographic system facilitates recovery of an amount of compound 5 which can be recycled to enhance the overall efficiency of the conversion of compound 5 to compound 14.

The next step is to convert the β-L-idopyranonitrile 14 into the new compound 3-O-benzyl-1,2-O-isopropylidene-β-L-idopyranuronamide 15, which represents a further aspect of the present invention. This conversion is preferably effected by oxidising the C5 cyano group of compound 14 to an amide group. A suitable oxidising agent is hydrogen peroxide which may be added in large molar excess (e.g. at least 10 molar equivalents, more preferably around 15 molar equivalents) compared to the amount of compound 14. The oxidation is preferably effected in the presence potassium carbonate, which may be provided in a slight molar excess compared to the amount of compound 14. A high yield of compound 15 can be obtained by reacting compound 14 with the oxidising agent for 1 to 3 hours, more preferably around 2 hours, at room temperature and then heating the reaction mixture to a temperature of 30 to 50° C., more preferably about 40° C., for around half an hour. Compound 15 can then be isolated by extraction into an organic phase, consisting of, for example, ethylacetate, washing the organic phase with water and then drying and removal of any residual solvents and crystallization from ethyl acetate/hexane. It will be appreciated that compound 15 represents a yet further example of a compound having the general formula 7 which can be converted as described below into a glycosyl donor or acceptor compound for use in the production of L-iduronate containing disaccharides and polysaccharides.

The final step in the above overall process to produce methyl 3-O-benzyl-1,2-O-isopropylidene-β-L-idopyranosyluronate, 12 from 3-O-benzyl-1,2-O-isopropylidene-α-L-idofuranonitrile 5 is conversion of the C5 amide group of compound 15 to an ester group. While this can be achieved using any appropriate conventional method, a preferred method is to add dimethylformamide dimethylacetal (DMF, DMA). The reaction of DMF, DMA with compound 15 may be carried out using an excess of DMF, DMA (e.g. 2 to 4, more preferably around 3, molar equivalents of DMF, DMA compared to the amount of compound 15) in an alcoholic solvent, such as methanol. The reaction is preferably effected over a time period of 4 to 8 hours, more preferably around 6 hours.

Compound 12 may then be isolated by extraction into a suitable organic phase (e.g. ethylacetate), washing of the organic phase with water, drying, removal of any solvents present and then column chromatography using an eluent such as 1:3 ethylacetate/hexane.

As stated above, methyl 3-O-benzyl-1,2-O-isopropylidene-β-L-idopyranosyluronate, 12 represents another example of a compound having the general formula 7 which can be used to produce L-iduronate containing disaccharides and polysaccharides. Compound 12 is also a high value intermediate in its own right. The above procedure for the production of this compound from compound 5 uses ambient or near ambient conditions, relatively low cost reagents and relatively simple crystallisation strategies for the isolation of the intermediate compounds 13, 14 and 15. This procedure therefore represents a commercially viable route to the commercially important compound 12 as well as two novel compounds 14 and 15.

Further preferred compounds of general formula 7 are compounds 12″ (compound 7 where X=OMe, $R^1=R^2=Ac$) and 12‴ (compound 7 where X=OMe, $R^1=R^2=Ac$, $R^3=Bn$), which can be used as glycosyl acceptor compounds (or donor compounds following appropriate modification) in the production of L-iduronate-containing disaccharides and polysaccharides as described in more detail below.

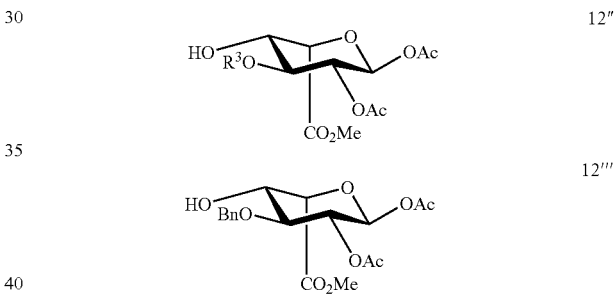

A simple and convenient method for producing compound 12″ from the cyanohydrin 5′ is via compound 7′ as shown below, which forms a further aspect of the present invention. The conversion of compound 7′ to compound 12″ represents a yet further aspect of the present invention.

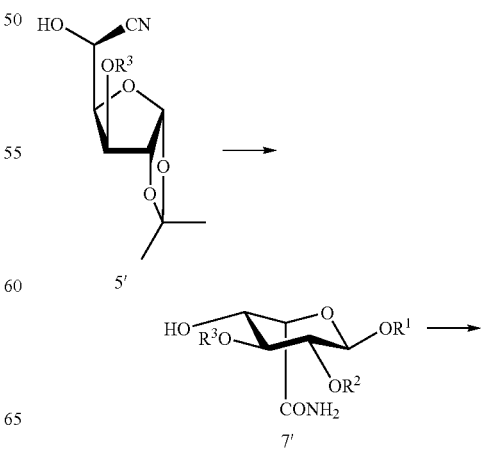

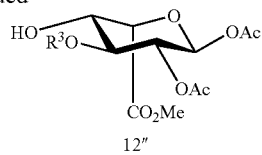

12″

Preferred embodiments of the above aspects of the invention provide a method for producing compound 12‴ from the cyanohydrin 5 via compound 8, and a method for producing compound 12‴ from compound 8.

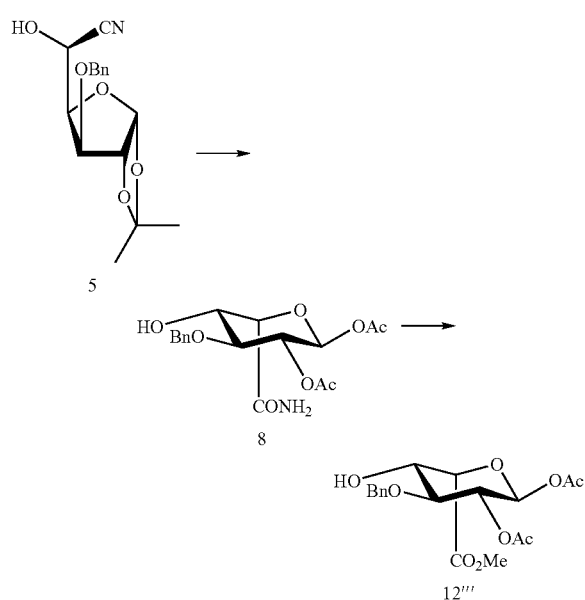

The first step in the above process can be carried out as hereinbefore described by deprotection of the C1 and C2 oxygen atoms to provide a mixture of compounds 9 and 10 followed by C1 and C2 acylation under appropriate conditions.

The second step in the process can then be carried out by the addition of a suitable nitrite (preferably amylnitrite) under acidic conditions (e.g. in the presence of acetic acid) followed by the addition of DMF/DMA. The nitrite is preferably added at room temperature and the reaction mixture then stirred for less than 5 hours after which the mixture is warmed to a temperature of less than around 100° C.

A particularly preferred process involves stirring the reaction mixture for 2 to 4 hours after addition of amylnitrite followed by warming the mixture to a temperature of around 80° C. After warming, the reaction mixture is preferably cooled to around room temperature at which point the DMF/DMA is added and the reaction mixture stirred at room temperature.

A significant advantage of this two step process over the four step process set out above for the conversion of compound 5 to compound 12 is that the above two step process enables the generation of ester glycosides (e.g. 12, 12′, 12″, 12‴) from cyanohydrins 5 and 5′ without the need to produce intermediate nitrile-bearing pyranosides (e.g. compounds 13 and 14). The two step process can also be carried out under relatively mild conditions using compounds of general formula 7 with free 4-OH groups.

A still further preferred aspect of the present invention provides an alternative route to making ester glycosides (represented generally by formula 12A) for use directly as glycosyl acceptor compounds (or donor compounds following further modification) from cyanohydrin 5′ by a single step process employing an alcohol ($R^{18}OH$) and an acid catalyst, such as an acid halide or mineral acid, as shown below. This single step process is an extremely convenient method for generating ester glycosides from cyanohydrins of the kind represented by formula 5′ and the process involves hydrolysis, esterification and glycosylation.

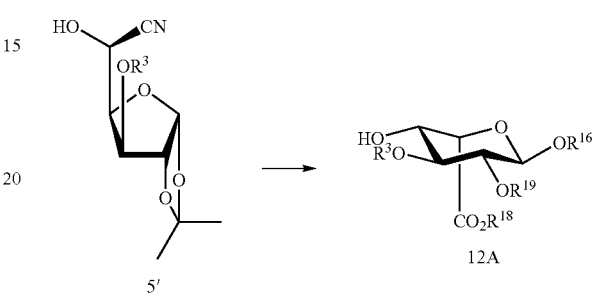

$R^{18}$ is a branched or unbranched, substituted or unsubstituted alkyl group, and $R^{19}$ is a protecting group. $R^{18}$ is preferably a $C_1$ to $C_6$ alkyl group, and $R^{18}$ is most preferably a methyl group or an ethyl group. $R^{18}$ at the C1 and C5 positions is provided by the initial alcohol $R^{18}OH$. $R^{19}$ may be any appropriate protecting group but is preferably an acetyl group, benzyl group or tetrahydropyranyl group.

The above process may generate a mixture of compound 12A and a related five-membered ring compound, from which the desired compound 12A can be isolated using any appropriate isolation strategy.

A preferred embodiment of the above process is shown below and involves the conversion of preferred cyanohydrin 5 to preferred ester iduronate glycoside derivative 12B by the addition of ethanol and acetyl chloride to compound 5.

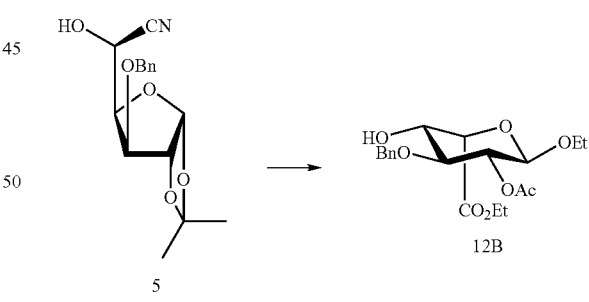

Having developed a number of relatively simple and convenient methods for producing various compounds falling within the general formula 7, any one of these compounds can be further processed to prepare an L-iduronate residue ready to be coupled to any one of a number of available monosaccharides to provide an L-iduronate-containing disaccharide containing a β(1→4)-glycosidic bond, as in the 'AB' glycosaminoglycan unit shown above in Schematic 1. Thus, a further aspect of the present invention provides a process for producing a disaccharide 16 from compound 7 as shown below

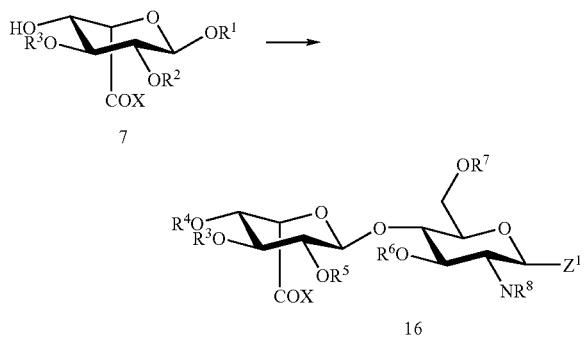

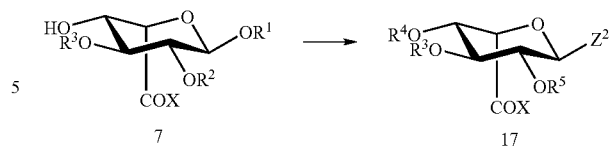

Where the C4 hydroxyl group is protected using any appropriate protecting group (e.g. $R^4$=acetyl, benzyl, tetrahydropyranyl (THP) etc) and the anomeric carbon atom is activated to make it susceptible to nucleophilic attack by the C4 hydroxyl group of compound 18 by replacing the $OR^1$ group with a leaving group, $Z^2$, which activates the anomeric carbon atom for glycosyl coupling, such as thiophenyl, trichloroacetimidate, fluoro, pentenyl, selenophenyl, aryl or alkyl sulfoxide, or sulfone.

As described above, a preferred compound of general formula 7 is 1,2-di-O-acetyl-3-O-benzyl-β-L-idopyranuronamide, 8. Compound 8 is converted into a preferred glycosyl donor compound 19 as shown below.

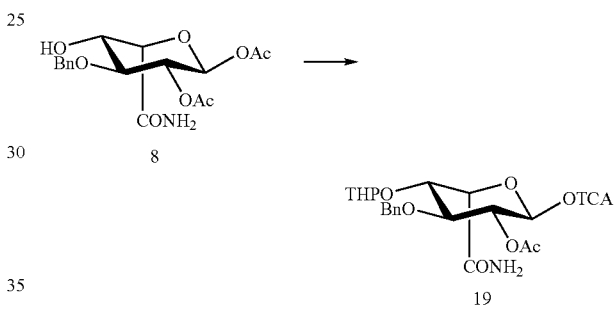

where $R^4$, $R^5$, $R^6$ and $R^7$ are the same or different protecting groups and $R^3$ and $R^4$ may be linked (e.g. by $R^3$ and $R^4$ forming part of a cyclic acetal group), X is selected from the group consisting of —$NH_2$, —OH and —OR, $NR^8$ is a nitrogen-containing protected amino group precursor, i.e. a group that will not be affected by the above conversion but which can be later converted to an amine group, for example $NR^8$ may be an azido ($N_3$) group, and $Z^1$ is a leaving group, such as thiophenyl, or a precursor to a leaving group, such as acetate or silyl ether which, after further modification, activates the anomeric carbon atom to which it is bonded to subsequent nucleophilic attack.

A preferred route to produce the disaccharide 16 from compound 7 requires conversion of compound 7 into a glycosyl donor compound 17 followed by coupling of compound 17 to a glycosyl acceptor compound 18 as shown below.

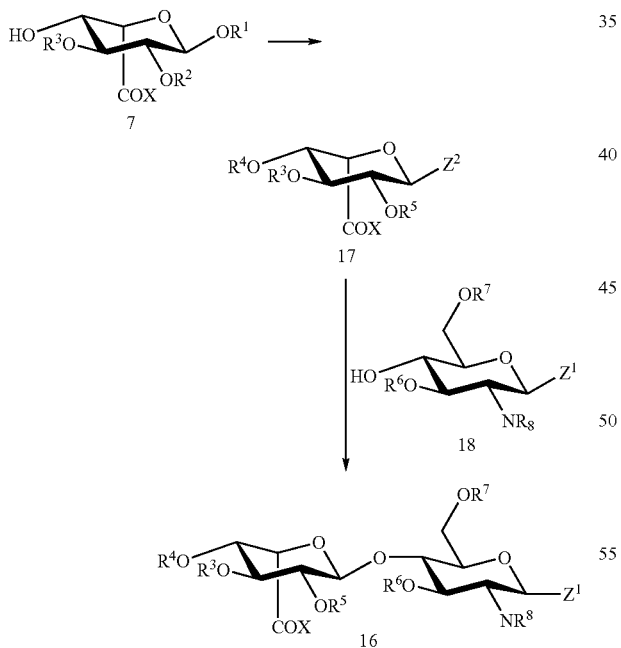

Where $Z^2$ is a leaving group which is displaced by the overall nucleophilic attack of the anomeric carbon atom of compound 17 by the oxygen atom of the C4 hydroxyl group of compound 18.

The first step in the above scheme is to convert compound 7 into a glycosyl donor compound 17 ready for coupling to the glycosyl acceptor compound 18, as illustrated below.

The C4 hydroxyl group of compound 8 is converted to an O-tetrahydropyranyl protecting group and the acetyl group bonded to the C1 oxygen atom is substituted with a trichloroacetimidate group.

An example of a group of glycosyl acceptor compounds which may be coupled to the glycosyl donor compound 7 is represented generically by compound 18 below, and a specific example of a preferred glycosyl acceptor compound is 2-azido-3,6-O-dibenzyl-1-thio-β-D-glucopyranoside 20.

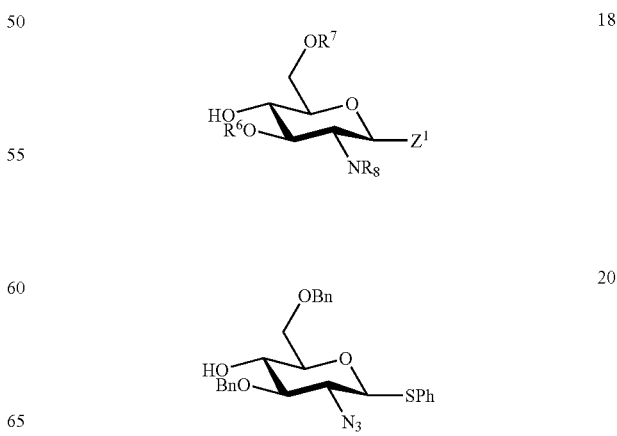

A preferred process for producing an L-iduronate containing disaccharide 21 from a preferred compound 8 is thus

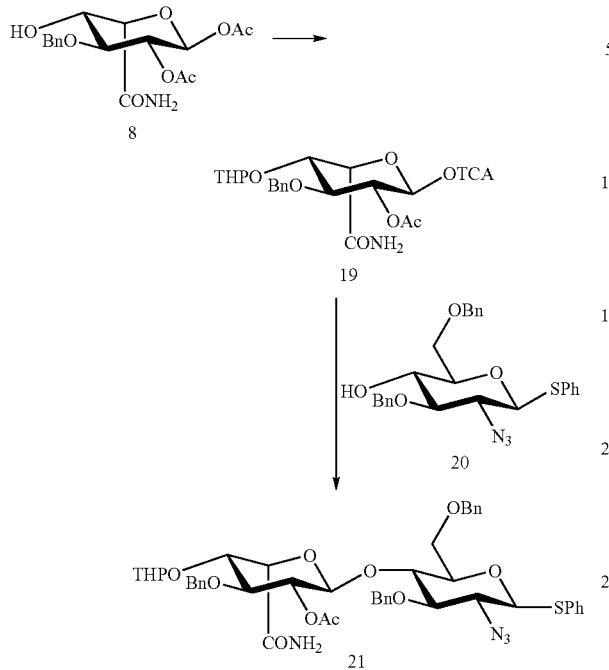

As described above, while compound 7 represents a preferred compound for use when making L-iduronate containing disaccharides, a suitable alternative compound is methyl 3-O-benzyl-1,2-O-isopropylidene-β-L-idopyranosyluronate (12). Since compound 12 contains a free C4 hydroxyl group and a protected anomeric carbon atom, to use compound 12 it must first be converted to a glycosyl donor compound 22 in a similar manner to compound 7, i.e. protection of the C4 hydroxyl group and activation of the anomeric carbon atom, as shown below.

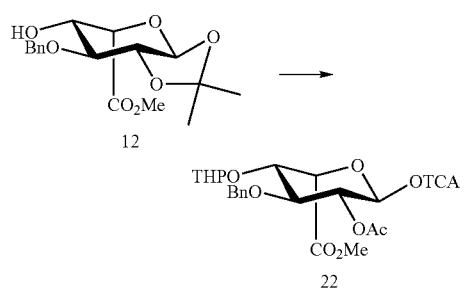

Once these transformations have been achieved, glycosyl donor compound 22 can then be coupled to any appropriate glycosyl acceptor compound (e.g. compound 18) in the same way as shown above for compound 7. If it is desired for the disaccharide product to include a different functional group at C5 to the ester group present in compound 22 then this can be achieved using any suitable method. For example, the C5 methyl ester functional group can be converted to an amide group by the addition of ammonia under suitable reactions conditions. It will be understood that this conversion can be performed at any convenient stage in the overall process to produce the disaccharide product. By way of example, an appropriate stage may be after the above transformation from compound 12 to compound 22 but before coupling to the glycosyl acceptor compound 18.

A further aspect of the present invention provides a method for the production of an esterified glycosyl donor compound 22' (compound 17 where $R^4$=ClCH$_2$C(O), $R^5$=Ac, $Z^2$=SPh) from the amide precursor compound 7".

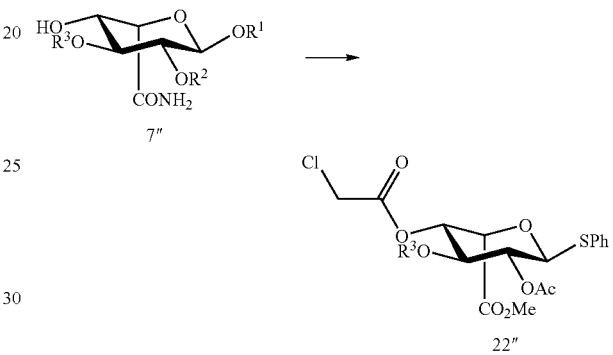

The above process is effected by addition of the chloroacetic acid protecting group to the free C4 hydroxyl group, conversion of the amide group to an ester group and activation of the C1 atom by addition of the thiophenyl group. It will be evident to the skilled person that the chloroacetic acid group and thiophenyl group are merely representative of a number of different C4 protecting groups and C1 activating groups which can be provided in the esterified glycosyl donor compound by appropriate modification to the process outlined above.

It is preferred that the amide group is converted to the ester group by the addition of a suitable nitrite (preferably amylnitrite) under acidic conditions (e.g. in the presence of acetic acid) followed by the addition of DMF/DMA. Employing these reagents in the process set out above represents a preferred embodiment of this aspect of the present invention as set out below in which compound 8 is converted to the esterified glycosyl donor compound 22'" (compound 17 where $R^3$=Bn, $R^4$=ClCH$_2$C(O), $R^5$—Ac, $Z^2$=SPh). Compound 22'" is an alternative to compound 22, and compound 22'" may be employed in saccharide coupling reactions in the same way as compound 22.

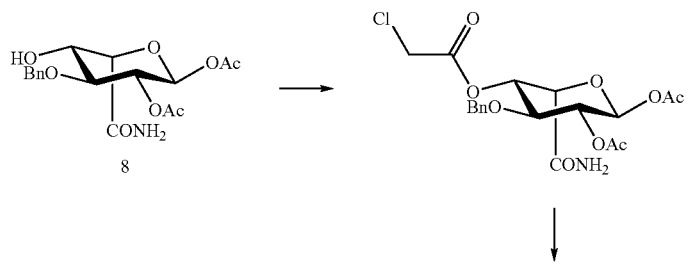

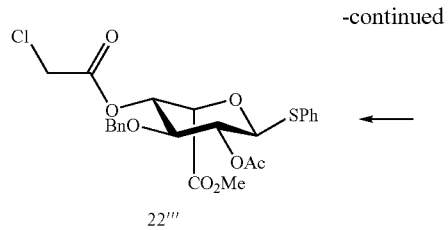
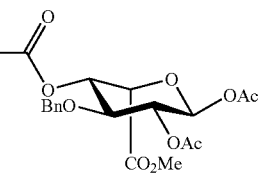

22‴

If desired, compound 22‴ can then be converted to an esterified glycosyl acetor compound simply be deprotecting the C4 hydroxyl group, for example by the addition of an organic base, such as benzylamine ($BnNH_2$).

It will be appreciated that if compound 7 is substituted for a compound which does not contain a free C4 hydroxyl group then the initial step of protecting the C4 hydroxyl group is no longer required. For example, if another of the above described alternative compounds to compound 7 was used, e.g. 1,2,3-tri-O-acetyl-3-O-benzyl-β-L-idopyranuronamide 11, then this compound could be converted to a glycosyl donor compound 23 simply by activating the anomeric carbon atom by the replacement of the acetyl group bonded to the C1 oxygen atom with a trichloroacetimidate group by selective 1-O-deacylation then conversion of the free 1-OH to the trichloroacetimidate, thus

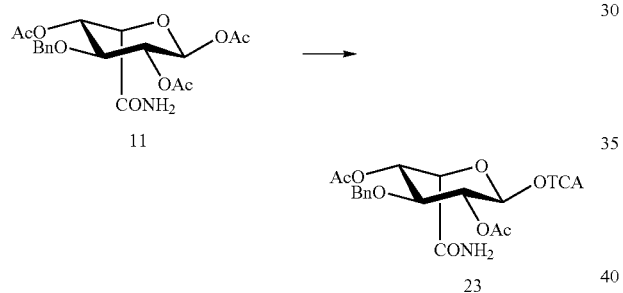

Once this transformation has been achieved, glycosyl donor compound 23 can then be coupled to any appropriate glycosyl acceptor compound (e.g. compound 18) in the same way as shown above for compound 7.

Another aspect of the present invention provides a process for converting a compound of formula 11' to a disaccharide of formula 16'

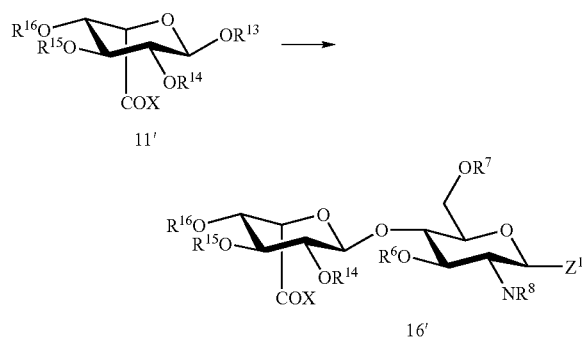

where $R^{13}$, $R^{14}$, $R^{15}$, $R^{16}$, $R^6$ and $R^7$ are the same or different protecting groups, X is selected from the group consisting of —$NH_2$, —OH and —OR, $NR^8$ is a nitrogen-containing protected amino group precursor, and $Z^1$ is a leaving group or a precursor to a leaving group, wherein the process comprises converting compound 11' to a glycosyl donor compound by activating the C1 carbon atom of compound 11' and then coupling said glycosyl donor compound to a glycosyl acceptor compound.

In addition to producing L-iduronate-containing disaccharides incorporating β(1→4)-glycosidic bonds, the present invention also provides a process for producing L-iduronate-containing disaccharides incorporating α(1→4)-glycosidic bonds, as in the 'BC' glycosaminoglycan unit shown above in Schematic 1. In this case, glycosyl acceptor compounds are produced for reaction with known glycosyl donor compounds. Thus, a further aspect of the present invention provides a process for producing a disaccharide 24 from compound 7 as shown below

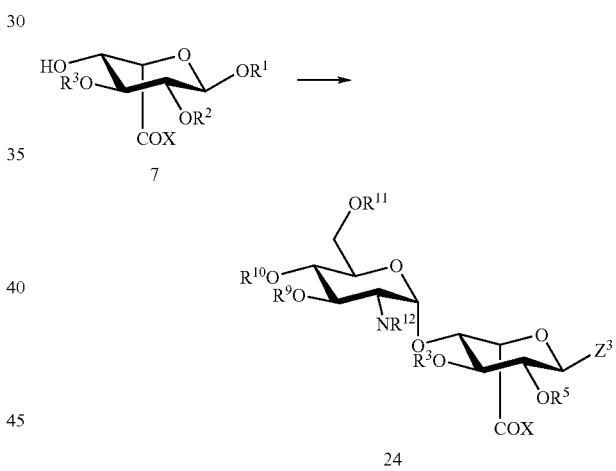

where, as above, $R^1$, $R^2$ and $R^3$ are the same or different protecting groups and $R^1$ and $R^2$ may be linked (e.g. by both $R^1$ and $R^2$ forming part of a cyclic acetal group), and X is selected from the group consisting of —$NH_2$, —OH and —OR, and where $R^9$, $R^{10}$ and $R^{11}$ are the same or different protecting groups and $R^9$ and $R^{10}$ may be linked (e.g. by $R^9$ and $R^{10}$ forming part of a cyclic acetal group), $NR^{12}$ is a nitrogen-containing protected amino group precursor, i.e. a group that will not be affected by the above conversion but which can be later converted to an amine group, for example $NR^{12}$ may be an azido ($N_3$) group, and $Z^3$ is a leaving group, such as thiophenyl, or a precursor to a leaving group, such as acetate or silyl ether which, after further modification, activates the anomeric carbon atom to which it is bonded to subsequent nucleophilic attack.

A preferred route to produce the α(1→4)-glycosidic bond containing disaccharide 24 from compound 7 requires coupling of a derivative of 7, i.e. compound 25 (a glycosyl acceptor), to a glycosyl donor compound 26 as shown below.

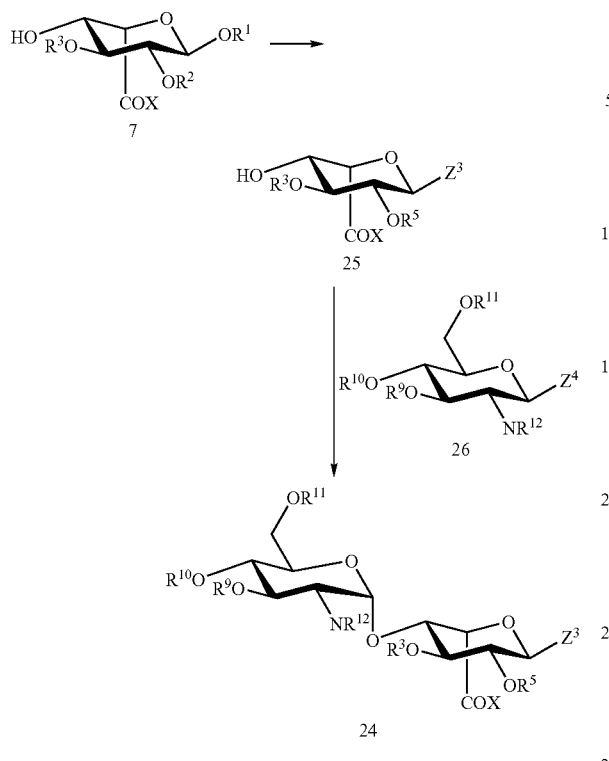

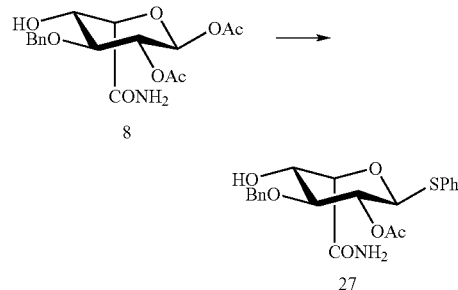

Compound 8 may be converted into a preferred glycosyl acceptor compound incorporating a C5 ester group rather than a C5 amide group. This may be achieved simply and conveniently by converting compound 8 to compound 22''' as hereinbefore described, followed by the addition of an organic base, such as BnNH$_2$, which deprotects the C4 hydroxyl group of compound 22''' to provide preferred compound 25' below.

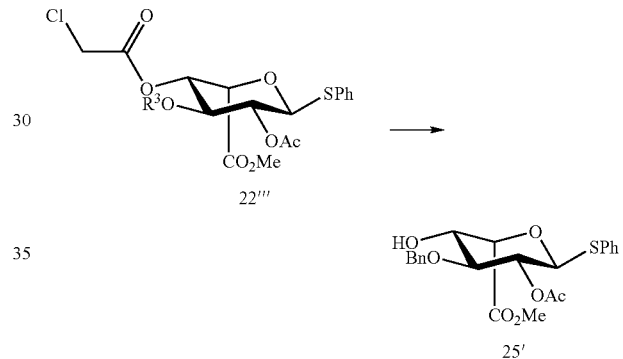

Where $Z^4$ is a leaving group which activates the anomeric carbon atom for glycosyl coupling, such as thiophenyl, trichloroacetimidate, fluoro, pentenyl, selenophenyl, aryl or alkyl sulfoxide, or sulfone. $Z^4$ is displaced by nucleophilic attack of the anomeric carbon atom of compound 26 by the oxygen atom of the C4 hydroxyl group of compound 25.

While compound 7 could be used as a glycosyl acceptor compound directly, it is preferable to convert it to a compound of general formula 25 prior to coupling to form the disaccharide since this ensures that the resulting disaccharide contains an anomeric carbon atom which can be readily activated for coupling to further disaccharides to form a polysaccharide. The conversion of the compound 7 into a glycosyl acceptor compound 25 is preferably achieved by modifying the anomeric carbon atom to make it susceptible to subsequent nucleophilic attack either directly or after further modification. This may be achieved by replacing the OR$^1$ group with an anomeric leaving group, $Z^3$, such as thiophenyl or a precursor to a leaving group, such as acetate or silyl ether which can be converted into a suitable leaving group, such as trichloroacetimidate.

An example of a group of glycosyl donor compounds which may be coupled to the glycosyl acceptor compound 7 is represented generically by compound 26 below, and a specific example of a preferred glycosyl acceptor compound is 2-azido-3-O-benzyl-4-O-p-methoxybenzyl-1-thio-β-D-glucopyranoside 28.

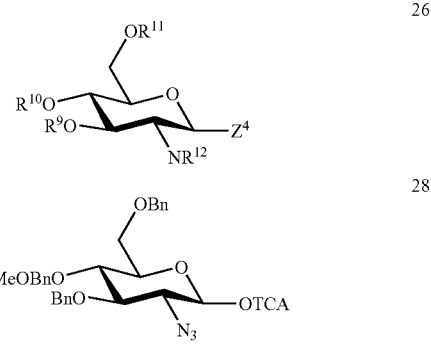

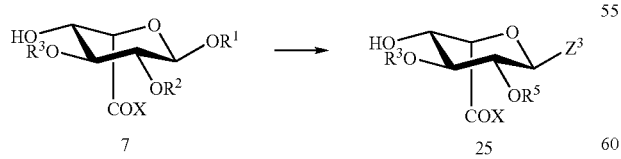

The preferred example of compound 7, 1,2-di-O-acetyl-3-O-benzyl-β-L-idopyranuronamide, 8 may be converted into a preferred glycosyl acceptor compound 27 by substituting the oxyacetyl group bonded to the anomeric carbon atom with thiophenyl group as indicated below.

In a preferred embodiment, a process for producing an L-iduronate containing disaccharide 29 from a preferred compound 8 is as follows.

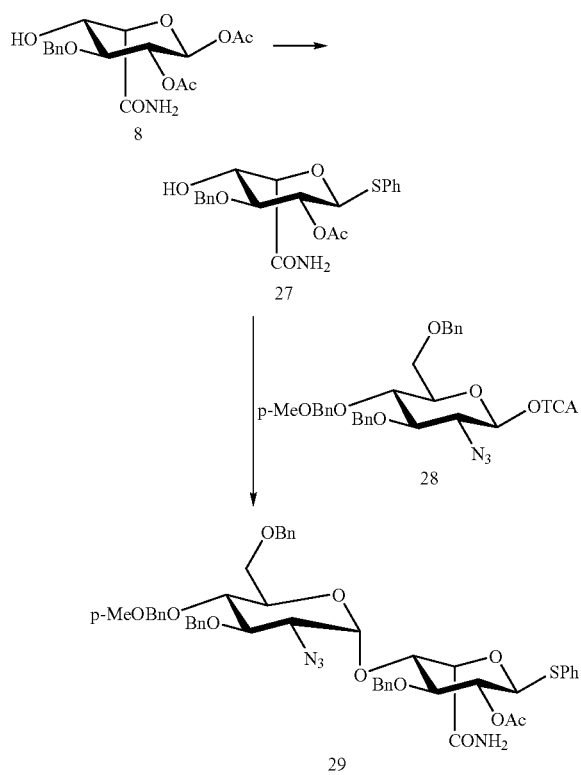

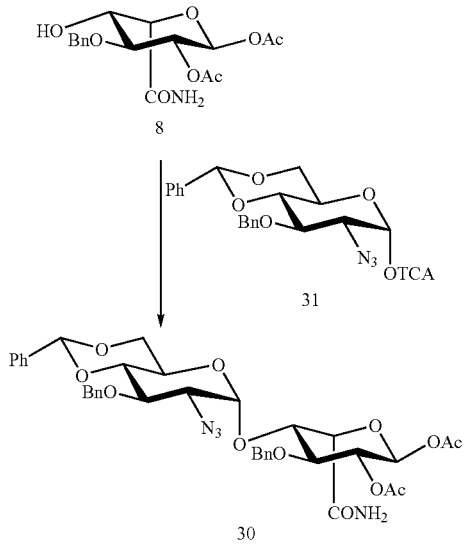

A further preferred embodiment provides a process for producing an L-iduronate containing disaccharide 2-azido-3-O-benzyl-4,6-O-benzylidene-2-deoxy-α-D-glucopyranosyl-(1→4)-1,2-di-O-acetyl-3-O-benzyl-β-L-idopyranuronamide 30 from the preferred compound 8. In this embodiment, disaccharide 29 is prepared directly from compound 8 without first activating the anomeric carbon atom of compound 8. Compound 30 is prepared by coupling compound 8 with 2-azido-3-O-benzyl-4,6-O-benzylidene-2-deoxy-α-D-glucopyranosyl trichloroacetimidate 31 as follows.

When making disaccharides of general formula 24 containing an α(1→4)-glycosidic bond, compound 7 can be substituted with 3-O-benzyl-1,2-O-isopropylidene-β-L-idopyranosyluronate 12 or derivatives of 1,2,3-tri-O-acetyl-3-O-benzyl-β-L-idopyranuronamide 11 with a free 4-OH. Since compound 12 contains a protected anomeric carbon atom it is preferably first converted to a suitable glycosyl acceptor compound by activation of the anomeric carbon atom. Moreover, as compound 11 contains a protected C4 hydroxyl group, this group must first be deprotected to yield a free hydroxyl group followed by activation of the anomeric carbon atom. Once these transformations have been achieved, the glycosyl acceptor compounds can then be coupled to any appropriate glycosyl donor compounds in the same way as shown above for compound 7. Transformation of the C5 ester group of compound 12 can be achieved using any suitable method as described above, e.g. addition of ammonia to convert the ester group to an amide group.

A still further aspect of the present invention provides a process for converting a compound of formula 11' to a disaccharide of formula 24'

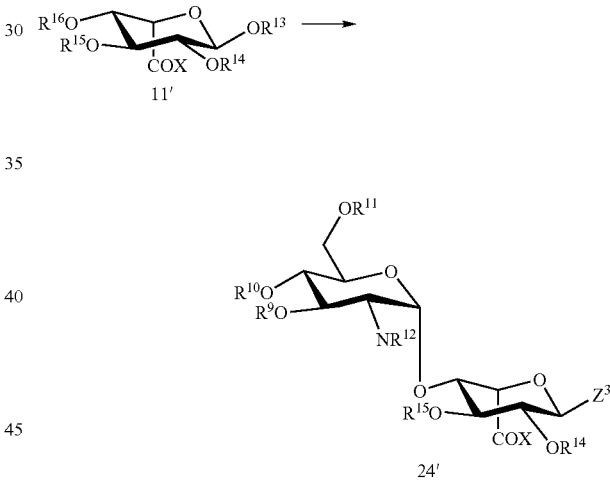

where $R^{13}$, $R^{14}$, $R^{15}$, $R^{16}$, $R^9$, $R^{10}$ and $R^{11}$ are the same or different protecting groups, X is selected from the group consisting of —$NH_2$, —OH and —OR, $NR^{12}$ is a nitrogen-containing protected amino group precursor, and $Z^3$ is a leaving group, wherein the process comprises converting compound 11' to a glycosyl acceptor compound by replacing the $R^{16}$ protecting group with a hydrogen atom and activating the C1 carbon atom of compound 11' and then coupling said glycosyl acceptor compound to a glycosyl donor compound.

A yet further aspect of the present invention provides a process for the production of an L-iduronate containing polysaccharide 32 (e.g. analogous to that shown in Schematic 1) from disaccharides of general formula 16 containing β(1→4)-glycosidic bonds as shown below.

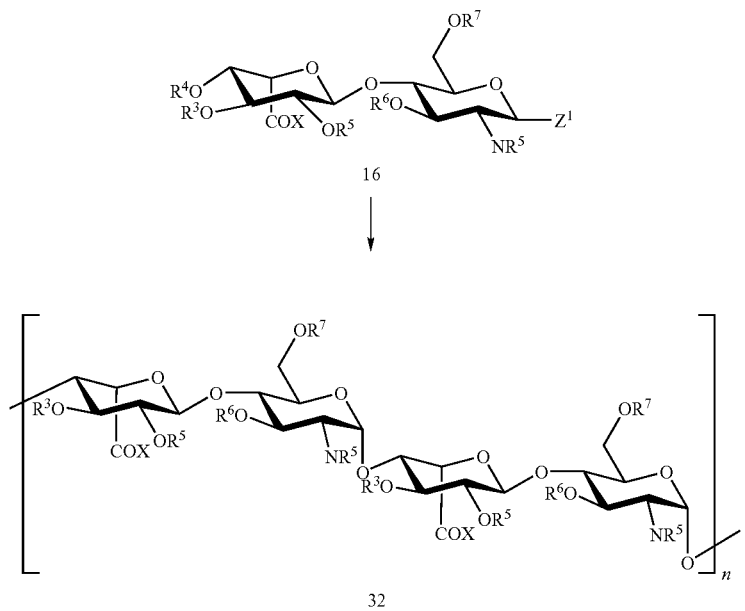

Where each group is as defined above in respect of formula 16. In order to effect the above coupling reaction it is necessary that the oxygen atom of the —$OR^4$ group can react with the anomeric carbon atom bonded to the $Z^1$ leaving group. In a preferred embodiment of this aspect of the invention, the —$OR^4$ group is first converted to a hydroxyl group prior to initiating the disaccharide coupling reaction.

The present invention further provides a process for producing a polysaccharide of formula 32' from a plurality of disaccharides of formula 16' where $R^{14}$, $R^{15}$, $R^6$ and $R^7$ are the same or different protecting groups, X is selected from the group consisting of —$NH_2$, —OH and —OR, $NR^8$ is a nitrogen-containing protected amino group precursor, $Z^1$ is a leaving group, and n is the number of repeating tetrasacharide units in the polysaccharide 32', in which each tetrasacharide unit consists of first and second coupled disaccharides 16', wherein the process comprises converting the $OR^{16}$ group of each disaccharide 16' to a hydroxyl group and then coupling the first and second disaccharides 16' by reacting the C4 oxygen atom of the first disaccharide 16' with the C1 carbon atom of the second disaccharide 16' to displace the $Z^1$ leaving group.

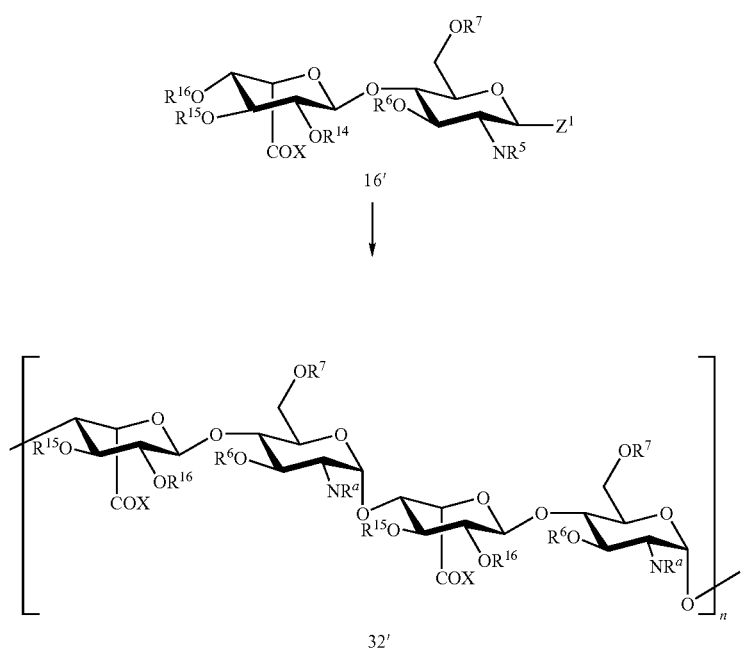

A still further aspect of the present invention provides a process for the production of an L-iduronate containing polysaccharide 33 from disaccharides of general formula 24 containing α(1→4)-glycosidic bonds, thus.

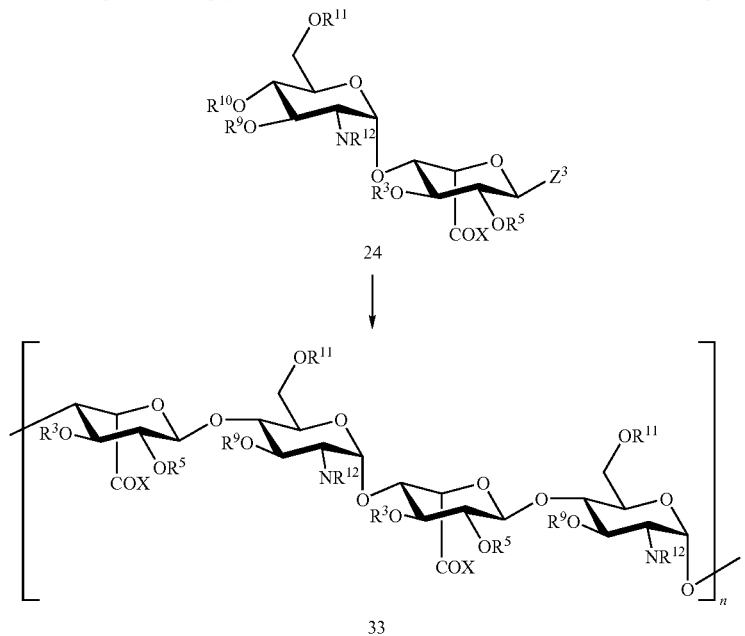

Where each group is as defined above in respect of formula 24. In a preferred embodiment of this aspect of the invention, the —$OR^{10}$ group is first converted to a hydroxyl group prior to initiating the disaccharide coupling reaction.

As described above, disaccharide 21 is a preferred example of the 'AB' type building block of general formula 16 (containing β(1→4) links) and disaccharide 29 is a preferred example of the 'BC' type building block of general formula 24 (containing α(1→4) links).

The present invention still further provides a process for the production of a polysaccharide of formula 33' from a disaccharide of formula 24'.

where $R^{14}$, $R^{15}$, $R^9$ and $R^{11}$ are the same or different protecting groups, X is selected from the group consisting of —$NH_2$, —OH and —OR, $NR^{12}$ is a nitrogen-containing protected amino group precursor, $Z^3$ is a leaving group, and n is the number of repeating tetrasaccharide units in the polysaccharide 33', in which each tetrasaccharide unit consists of first and second coupled disaccharides 24', wherein the process comprises converting the $OR^{10}$ group of each disaccharide 24' to a hydroxyl group and then coupling the first and second disaccharides 24' by reacting the C4 oxygen atom of the first disaccharide 24' with the C1 carbon atom of the second disaccharide 24' to displace the $Z^3$ leaving group.

Coupling of a plurality of units of the same type of disaccharide building block, e.g. disaccharide 21 or disaccharide 29, would produce the polysaccharide 34, which represents a preferred example of polysaccharides 32/32' and 33/33'.

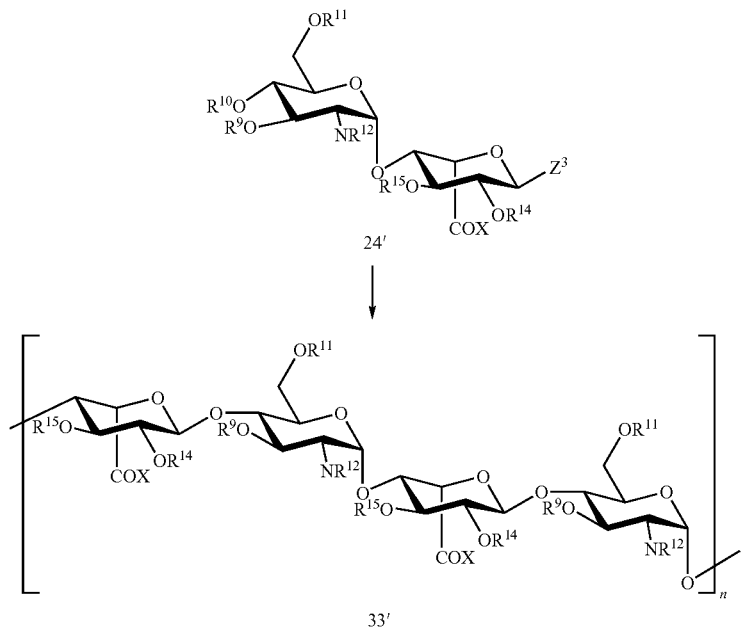

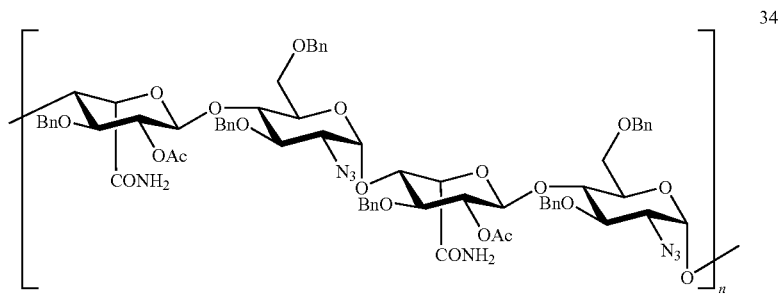

34

Polysaccharides 32, 32', 33, 33' and 34 can then be further derivatised, for example by replacement of certain protecting groups with sulphate groups to produce heparin-type polysaccharides as shown in Schematic 1.

A further preferred polysaccharide 34' in which the C5 group is an ester function rather than an amide function (as in compound 34) is shown below.

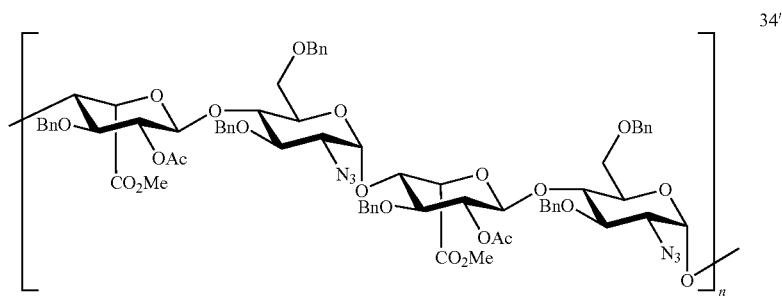

34'

Compound 34' may be produced using the methods described above.

Any of the disaccharide compounds presented hereinbefore which incorporate a 1-OAc group may be converted to an activated glycosyl donor compound by the addition of an organic acid, such as $BnNH_2$, followed by treatment with a suitable activating agent, e.g. TCA, SPh etc. $BnNH_2$ is particularly preferred because it has been shown to selectively remove the 1-OAc group.

Moreover, any of the disaccharide compounds set out above which incorporate protected C4 oxygen atoms may be deprotected using a suitable deprotection procedure to provide a free C4 hydroxyl group, making the deprotected disaccharide compound a candidate for use as a glycosyl acceptor group.

Thus, a first portion of a disaccharide 35 may be converted into a glycosyl donor compound 35' and a second portion of disaccharide 35 may be converted into a glycosyl acceptor compound 35". The donor and acceptor compounds 35', 35" may then be reacted together to produce a tetrasaccharide 34" incorporating two of the same disaccharide units. A preferred example of this process is set out below in which a tetrasaccharide 34" is produced which has the same repeating structure as preferred polysaccharide 34' above.

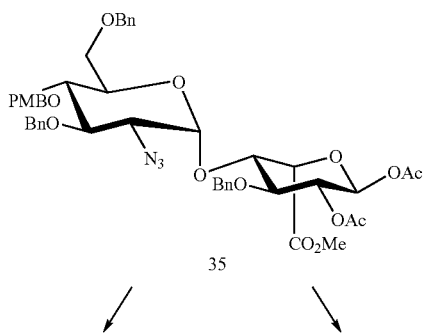

35

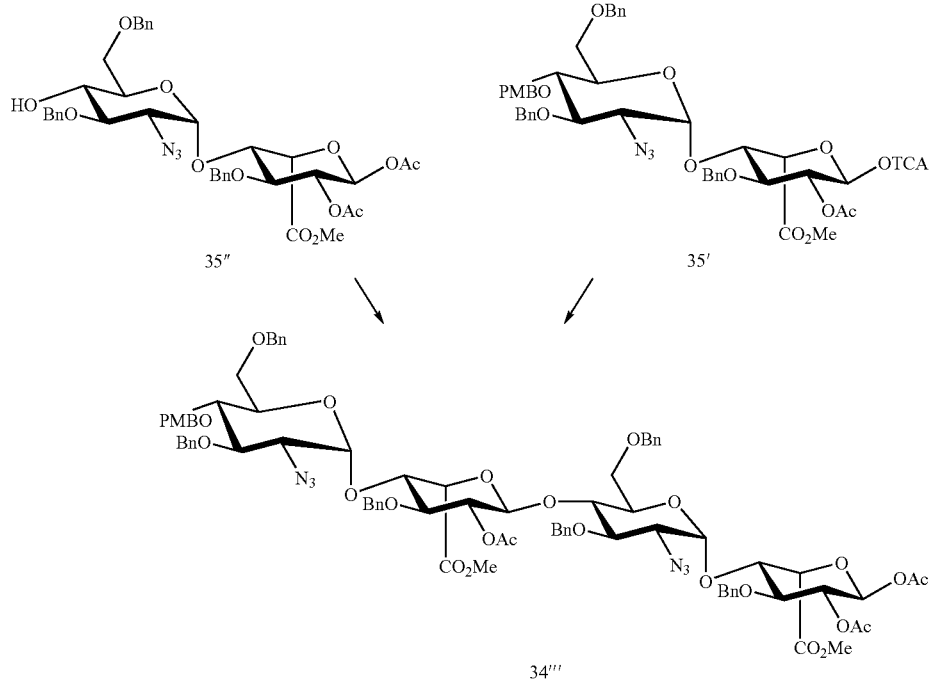

The present invention provides a number of commercially viable syntheses of L-iduronate type compounds using relatively inexpensive reagents under ambient conditions. This work provides new scalable routes to prepare the novel β-L-idopyranuronamide compounds 8 and 11 as well as a new, commercially feasible method for the production of a high value compound, 12 together with other novel intermediate compounds. These compounds can then be used in the production of core disaccharide building blocks for heparin-type polysaccharides as shown below in Reaction Scheme I. This work therefore has very significant market potential for an entirely new class of medicinal drugs that promote or inhibit the function of heparan sulfate/heparin which could potentially be used in a number of diseases that affect the general population.

Reaction Scheme I

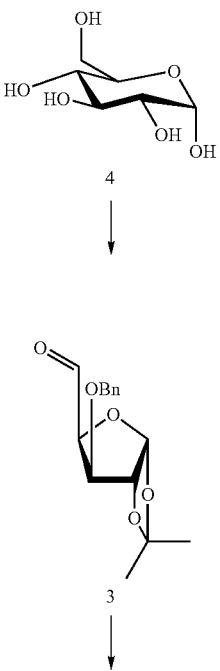

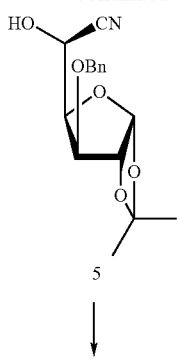
↓
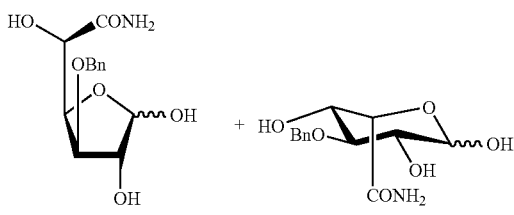
↓
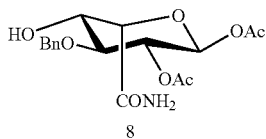
↓
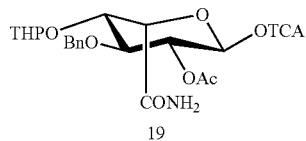
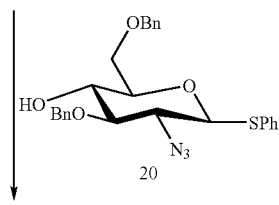
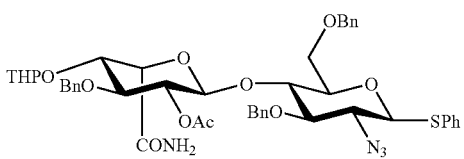
↓

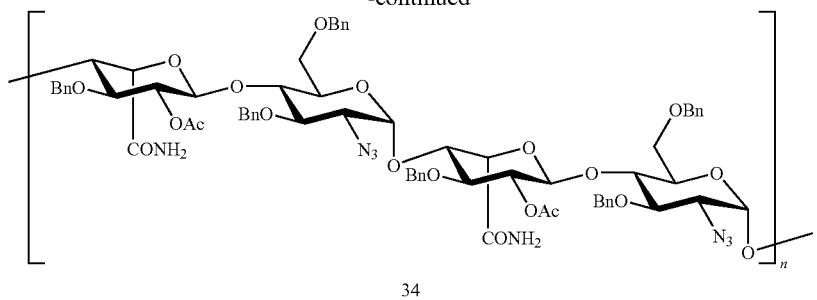

34

The invention will be further described by way of example only with reference to the following non-limiting Examples.

EXAMPLE

An L-iduronate containing polysaccharide 34 has been prepared from α-D-glucose 4 according to Reaction Scheme I as follows.

Conversion of α-D-Glucose 4 to 3-O-Benzyl-1,2-O-isopropylidene-α-D-Xylo-Dialdose 3 a) Production of 1,2:5,6-Di-O-isopropylidene-α-D-glucose[11]. To 305 g (1.69 mol) of powdered D-glucose in 2.5 L of acetone (99.9%) is added 500 g (3.67 mol) of anhydrous $ZnCl_2$ and 12 g (0.047 mol) of iodine. The mixture is stirred for 16 hrs at RT and then 5 hrs at reflux. It is then neutralised with 50% NaOH solution (336 g in 330 mL) and addition of sodium thiosulphate solution (23 g). The precipitated salts are filtered off through celite and the precipitate washed with acetone three times. The acetone is evaporated and the residue redissolved in dichloromethane and washed with water two times. After drying with $MgSO_4$ and evaporation of the organic phase the desired product is crystallised from boiling hexane. This yields 185.3 g (42%).

b) Production of 3-O-Benzyl-1,2:5,6-di-O-isopropylidene-α-D-glucose[12]. To 377 g (1.45 mol) of 1,2:5,6-Di-O-isopropylidene-α-D-glucose is added 180 mL (1.56 mol) of BnCl, 17 g $Bu_4NHSO_4$, 200 g NaOH dissolved in 200 mL of water and 800 mL THF. The mixture is stirred for 3 hrs at reflux. The phases were separated and the aqueous phase extracted with diethylether. The organic phase was dried with $MgSO_4$ and evaporated.

c) Production of 3-O-Benzyl-1,2-O-isopropylidene-α-D-glucose[13]. To the crude from above is added 800 mL of AcOH and 200 mL water and heated to 60 degrees C. for 6 hrs. Then the solvents are evaporated and the residue evaporated with toluene three times.

d) Production of 3-O-Benzyl-1,2-O-isopropylidene-α-D-xylo-dialdose 3[13]. To the crude from above is added 433 g (1.88 mol) of $KIO_4$ in 800 mL EtOH and 200 mL of water and cooled in an ice bath in the beginning. Stirred for 2 hrs at RT, then filtered and the EtOH evaporated. The residue was redissolved in dichloromethane and washed with water. The organic phase was dried with $MgSO_4$ and evaporated. The crude aldehyde from these 3 steps was used without further purification for the formation of the ido cyanohydrin 3.

Conversion of Dialdose 3 to 3-O-Benzyl-1,2-O-isopropylidene-α-L-Idofuranonitrile 5

3-O-benzyl-1,2-O-isopropylidene-α-L-idofuranonitrile 5 was prepared by converting the dialdose 3 to a mixture of L-idofuranonitriles 5 and 6 and then isolating L-idofuranonitrile 5.

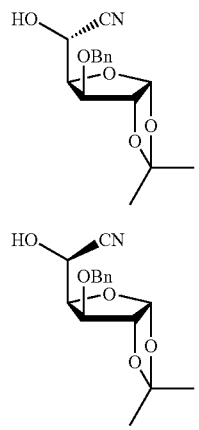

To the crude compound 3 was added ethanol (1.5 L), water (1.5 L), $MgCl_2.6H_2O$ (295 g, 1.59 mol) and KCN (94 g, 1.59 mol). After a few minutes a precipitate started to form and the mixture was stirred for 5 days at room temperature. The product mixture was then filtered and $CH_2Cl_2$ added to dissolve the product. The organic phase was separated, dried with $MgSO_4$ and evaporated. The crystalline product isolated was a 3:1 mixture of compounds 5 and 6. The total mass of the crystalline product obtained was 335.3 g (76%). Compound 5 was obtained by crystallisation by dissolving the product mixture in THF (1 vol) and adding hexane (3 vols). This yielded 223.7 g (51%) of compound 5. The residual material was recycled through re-equilibration by the addition of $MgCl_2.6H_2O$ (0.1 mol eq.) and KCN (0.1 mol eq.) which produced a further 88.9 g of compound 5. The total amount of compound 5 obtained was 312 g (71%).

Conversion of L-Idofuranonitrile 5 to 1,2-Di-O-Acetyl-3-O-Benzyl-β-L-Idopyranuronamide 8

The β-L-idopyranuronamide 8 was produced from the α-L-idofuranonitrile 5 via formation of a mixture of 5- and 6-membered ring compounds 9 and 10 as shown in Reaction Scheme I. The mixture of compounds 9 and 10 was converted directly to compound 8 without isolating either compound 9 or 10 from the mixture.

The conversion of the aldehyde 5 to the mixture of compounds 9 and 10 was effected by reacting aldehyde 5 with aqueous HCl (30%) at room temperature as follows. To 55.7 g (0.182 mol) of 5 was added 550 mL of HCl (32%). The mixture, which slowly dissolved, was stirred for 3 hrs at room temperature. The solution was neutralised by addition of $NaHCO_3$ in portions during 2 hours. The residue was then extracted 3 times with THF (300 mL). The organic phase was dried with MgSO$_4$, filtered and evaporated to yield 35 g. Stirring the crude with CHCl$_3$ (300 mL) gave 27.2 g of 9 and 10 as a precipitate (53%).

Production of compound 8 from the mixture of compounds 9 and 10 proceeded as follows. To 25.7 g (0.091 mol) of the mixture of compounds 9 and 10 was added CH$_2$Cl$_2$ (250 mL) and then Ac$_2$O (19 mL, 0.20 mol) and DMAP (220 mg, 1.82 mmol). The mixture was stirred for 6 hours and then washed with NaHCO$_3$ (sat., 200 mL), HCl (100 mL, 1%) added, dried with MgSO$_4$ and evaporated to give 34 g of crude compound 8. The crude product 8 was purified by crystallization by dissolving the crude product 8 in ethylacetate (250 mL) and adding hexane (250 mL). The resultant precipitate was filtered and recrystallization yielded 12.6 g of pure compound 8 (38%). The remaining material was recycled to compound 5 by dissolving the material in MeOH and adding a catalytic amount of sodium, which yielded 15 g of compound 5.

Conversion of L-Idopyranuronamide 8 to Glycoside Donor Compound 19

The C4 hydroxyl group of compound 8 is converted to an O-tetrahydropyranyl protecting group and the acetyl group bonded to the C1 oxygen atom is substituted with a trichloroacetimidate group.

a) Preparation of 1,2-Di-O-acetyl-3-O-benzyl-4-O-tetrahydropyranyl-β-L-idopyranuronamide. To 1.01 g (2.75 mmol) of 8 was added 20 mL of dry CH$_2$Cl$_2$, 1 mL (11.0 mmol) dihydropyran and 5 mg (0.027 mmol) p-toluenesulphonic acid monohydrate at 0° C. The mixture was stirred for 2 hours and then washed with NaHCO$_3$ (sat.) 20 mL, dried with MgSO$_4$ and evaporated. Column chromatography using EtOAc/hexane 1:1 as eluent yielded 921 mg of the idopyranuronamide product (74%).

b) Preparation of 2-O-acetyl-3-O-benzyl-4-O-tetrahydropyranyl-β-L-idopyranuronamide. To 790 mg (1.75 mmol) of the above product was added 8 mL of dry THF and 0.2 mL (1.84 mmol) BnNH$_2$ The mixture was stirred for 20 hours and evaporated. Column chromatography using EtOAc/hexane 2:1 as eluent yielded 438 mg of the THP ether (61%).

c) Preparation of 2-O-acetyl-3-O-benzyl-4-O-tetrahydropyranyl-β-L-idopyranuronamide trichloroacetimidate (19). To 438 mg (1.07 mmol) of the above THP ether was added 5 mL of dry CH$_2$Cl$_2$, 1 mL (10 mmol) trichloroacetonitrile and catalytic amount of DBU. The mixture was stirred for 2 hours and evaporated. Column chromatography using EtOAc/hexane 1:1 containing NEt$_3$ 1% as eluent yielded 393 mg of 19 (66%).

Production of 2-O-Acetyl-3-O-benzyl-4-O-tetrahydropyranyl-α-L-idopyranuronamidyl-(1→4)-phenyl-2-azido-3,6-O-dibenzyl-1-thio-β-D-glucopyranoside 21 from Glycoside Donor Compound 19

To 265 mg (0.55 mmol) of phenyl 2-azido-3,6-O-dibenzyl-1-thio-β-D-glucopyranoside and 383 mg (0.69 mmol) of compound 19 was added dry CH$_2$Cl$_2$ (2 mL). To this solution, stirred under N$_2$, was added first TMSOTf (0.01 eq. as a solution in CH$_2$Cl$_2$) and then after 90 minutes another 4 μL (0.04 eq.). The reaction was then quenched after a further 30 minutes with NEt$_3$ and solvents removed in vacuo. Column chromatography (EtOAc/hexane 2:3) yielded 176 mg of disaccharide 21 (36%).

Production of Polysaccharide 34 from Disaccharide 21

Disaccharides 21 were coupled together using established methodologies to produce polysaccharide 34.

Synthetic Methods

Production of Alternative to Disaccharide 29

As mentioned above, an alternative to preferred disaccharide 29 is 2-Azido-3-O-benzyl-4,6-O-benzylidene-2-deoxy-α-D-glucopyranosyl-(1→4)-1,2-di-O-acetyl-3-O-benzyl-β-L-idopyranuronamide 30. Set out below is a method for the production of disaccharide 30 from L-Idopyranuronamide 8.

To 110 mg (0.21 mmol) of 2-azido-3-O-benzyl-4,6-O-benzylidene-2-deoxy-D-glucopyranosyl trichloroacetimidate and 51 mg (0.14 mmol) of compound 8 was added dry CH$_2$Cl$_2$ (1 mL) and 100 mg powdered molecular sieves 3 Å under N$_2$. After stirring for 30 minutes the mixture was cooled to –30° C. and TMSOTf (4 μL, 0.02 mmol) added. The mixture was allowed to warm to room temperature during 1 hour, quenched with NEt$_3$ and solvents removed in vacuo. Column chromatography (EtOAc/hexane 1:1) yielded 22 mg of disaccharide 30 (22%).

Production of L-Idopyranosyluronate 12

As described above, the L-idopyranosyluronate 12 is commercially important in its own right and represents an alternative to compound 8 for use in coupling reactions to produce L-iduronate containing disaccharides and polysaccharides. Presented below is a method for the production of compound 12 from L-Idofuranonitrile 5, which may be produced from α-D-Glucose 4 or 3-O-Benzyl-1,2-O-isopropylidene-α-D-Xylo-Dialdose 3 as set out in the above Example.

Conversion of L-Idofuranonitrile 5 to 3-O-Benzyl-L-idopyranonitrile 13

To 16.6 g (0.054 mol) of compound 5 was added trifluoroacetic acid (60 mL) and water (25 mL), and the mixture stirred for 30 min. The solvents were removed in vacuo, water (30 mL) was added and then removed in vacuo. The residue was dissolved in ethylacetate (150 mL), dried using MgSO$_4$ and filtered. To the resulting solution was added hexane (150 mL) and standing overnight led to crystallisation yielding 11.4 g of compound 13 (79%).

Conversion of L-idopyranonitrile 13 to 3-O-Benzyl-3-O-Benzyl-1,2-O-isopropylidene-β-L-idopyranonitrile 14

To 1.06 g (4.0 mmol) of compound 13 was added dry THF (20 mL), 2-methoxy-propene (2 mL, 20 mmol) and camphorsulphonic acid (20 mg, 0.08 mmol). The mixture was stirred for 36 hours and then quenched with NEt$_3$. After removal of solvents, column chromatography (EtOAc/hexane 1:3) yielded 1.2 g of 3-O-benzyl-1,2-O-isopropylidene-4-O-(2-methoxy-isopropyl)-β-L-idopyranonitrile (80%).

To 1.1 g (2.92 mmol) of 3-O-benzyl-1,2-O-isopropylidene-4-O-(2-methoxy-isopropyl)-β-L-idopyranonitrile was added dry THF (10 mL) and p-toluenesulphonic acid monohydrate (55 mg, 0.29 mmol). The mixture was stirred for 18 hour and then quenched by addition of NEt$_3$. After removal of solvents, column chromatography (EtOAc/hexane 1:3) yielded 795 mg of compound 14 (64%) and 150 mg of compound 5 (12%).

Conversion of L-Idopyranonitile 14 to 3-O-Benzyl-1,2-O-Isopropylidene-β-L-Idopyranuronamide 15

To 795 mg (2.61 mmol) of compound 14 was added 1,4-dioxane (20 mL), water (10 mL), $K_2CO_3$ (400 mg, 2.9 mmol) and $H_2O_2$ (5 mL, 39 mmol, 27%). After stirring for 2 hours the solution was heated to 40° C. for 30 min., extracted with ethylacetate, the organic phase washed with water, dried using $MgSO_4$ and solvents removed in vacuo to afford 803 mg of compound 15 (95%).

Conversion of L-Idopyranuronamide 15 to Methyl 3-O-Benzyl-1,2-O-isopropylidene-β-L-idopyranosyluronate 12

To 738 mg (2.28 mmol) of compound 15 was added dry MeOH (8 mL) and DMF dimethylacetal (0.9 mL, 6.8 mmol). After stirring for 6 hours the solution was extracted with ethylacetate, the organic phase washed with water, dried using $MgSO_4$ and solvents removed in vacuo. Column chromatography (EtOAc/hexane 1:3) yielded 576 mg of compound 12 (75%).

Production of Further Alternative to L-Idopyranuronamide 8

1,2,3-Tri-O-acetyl-3-O-Benzyl-β-L-idopyranuronamide 11 represents a further alternative to compound 8 for use in coupling reactions to produce L-iduronate containing disaccharides and polysaccharides. Presented below is a method for the production of compound 11 from compound 10, which may be isolated from a mixture of compounds 9 and 10 produced from α-D-Glucose 4 as set out in the above Example.

To 146 mg (0.51 mmol) of powdered compound 10 was added $CH_2Cl_2$ (5 mL) and then pyridine (0.25 mL) and $Ac_2O$ (0.25 mL). The mixture was stirred for 90 minutes, evaporated and the residue then purified by column chromatography using EtOAc/hexane 1:1 as eluent yielding 163 mg of crystalline compound 11 (77%).

Alternative Method for Producing L-Idofuranonitrile 5

An alternative method for the production of L-Idofuranonitrile 5 employing recycling of the product mixture is now described.

From 38 g of a 2:1 mixture of compounds 5 and 6 was crystallised 19 g of pure 5. The remaining material (a 1:2 mixture of compounds 5 and 6) was re-equilibrated by the addition of 0.1 molar equivalents of KCN and $MgCl_2$ to yield 17 g of a 20:1 mixture of compounds 5 and 6.

Alternative Methods for Producing L-Iduronate Containing Disaccharides

Preparation of Precursor to Disaccharide Glcosyl Donor/Acceptor

The disaccharide 2-Azido-3-O-benzyl-4-O-p-methoxybenzyl-6-O-acetyl-2-deoxy-α-D-glucopyranosyl-(1→4)-methyl 1,2-di-O-acetyl-3-O-benzyl-β-L-idopyranuronate of general formula 24 (where $Z^3$=Ac, $NR^{12}$=$N_3$, $R^9$=Bn, $R^{10}$=PMB, $R^{11}$=Ac, X=OMe, $R^3$=Bn, $R^5$=Ac) was prepared as follows.

To 2.22 g (3.69 mmol) of the trichloroacetimidate azido donor 26 (where $Z^4$=OTCA, $NR^{12}$=$N_3$, $R^9$=Bn, $R^{10}$=PMB, $R^{11}$=Ac) and 1.21 g (3.17 mmol) of the iduronic ester acceptor 12''' was added dry toluene and solvents evaporated twice. The residue was dried for 2 h, then placed under Argon and 20 mL of dry DCM was added. The solution was cooled to −25° C. and TMSOTf (7 μL (0.039 mmol) was added dropwise using a microsyringe. The mixture was kept at this temperature for 1 h and then quenched with two drops of $NEt_3$. The solvent was evaporated and column chromatography using yielded 1.74 g (67%) of the disaccharide.

The disaccharide produced above was then used to prepare the following glycosyl donor/acceptor compounds.

Preparation of Disaccharide Glycosyl Donor

The disaccharide 2-Azido-3-O-benzyl-4-O-p-methoxybenzyl-6-O-acetyl-2-deoxy-α-D-glucopyranosyl-(1→4)-methyl 2-O-acetyl-3-O-benzyl-L-idopyranuronate of general formula 24 (where $Z^3$=OH, $NR^{12}$=$N_3$, $R^9$=Bn, $R^{10}$=PMB, $R^{11}$=Ac, X=OMe, $R^3$=Bn, $R^5$=Ac) was prepared as follows.

To 1.63 g (1.98 mmol) of the disaccharide precursor prepared above of general formula 24 (where $Z^3$=Ac, $NR^{12}$=$N_3$, $R^9$=Bn, $R^{10}$=PMB, $R^{11}$=Ac, X=OMe, $R^3$=Bn, $R^5$=Ac) was added ether (30 mL) and the solution was cooled to 0° C. Then $BnNH_2$ (1 mL, 9.17 mmol) was added and the mixture was stirred for 3 h. EtOAc was added and the organic phase was washed with 1M HCl and then $NaHCO_3$ (sat.). The organic phase was dried ($MgSO_4$), solvents removed and column chromatography yielded 838 mg (54%) of the disaccharide.

Preparation of Disaccharide Glycosyl Acceptor

The disaccharide 2-Azido-3-O-benzyl-6-O-acetyl-2-deoxy-α-D-glucopyranosyl-(1→4)-methyl 1,2-di-O-acetyl-3-O-benzyl-β-L-idopyranuronate of general formula 24 (where $Z^3$=Ac, $NR^{12}$=$N_3$, $R^9$=Bn, $R^{10}$=H, $R^{11}$=Ac, X=OMe, $R^3$=Bn, $R^5$=Ac) was prepared as follows.

To 370 mg (0.45 mmol) of the disaccharide precursor prepared above of general formula 24 (where $Z^3$=Ac, $NR^{12}$=$N_3$, $R^9$=Bn, $R^{10}$=PMB, $R^{11}$=Ac, X=OMe, $R^3$=Bn, $R^5$=Ac) was added a 20:1 mixture of $DCM/H_2O$ (5 mL) and DDQ (150 mg, 0.67 mmol). The mixture was stirred 1 h, filtered, solvents removed and column chromatography 268 mg (85%) of the disaccharide.

Preparation of Disaccharide Glycosyl Donor

The disaccharide 2-Azido-3-O-benzyl-4-p-methoxybenzyl-6-O-acetyl-2-deoxy-α-D-glucopyranosyl-(1→4)-methyl 2-O-acetyl-3-O-benzyl-L-idopyranuronate trichloroacetimidate of general formula 24 (where $Z^3$=OTCA, $NR^{12}$=$N_3$, $R^9$=Bn, $R^{10}$=PMB, $R^{11}$=Ac, X=OMe, $R^3$=Bn, $R^5$=Ac) was prepared as follows.

To 781 mg (1.00 mmol) of the disaccharide precursor prepared above of general formula 24 (where $Z^3$=Ac, $NR^{12}$=$N_3$, $R^9$=Bn, $R^{10}$=PMB, $R^{11}$=Ac, X=OMe, $R^3$=Bn, $R^5$=Ac) was added dry DCM (10 mL), trichloroacetonitrile (0.7 mL, 7.0 mmol) and DBU (10 μL, 0.07 mmol). The mixture was stirred 1 h, solvents removed and column chromatography yielded 796 mg (86%) of the imidate.

Preparation of Alternative Precursor to Disaccharide Glcosyl Donor/Acceptor

The disaccharide 2-Azido-3,6-di-O-benzyl-4-O-p-methoxybenzyl-2-deoxy-α-D-glucopyranosyl-(1→4)-methyl 1,2-di-O-acetyl-3-O-benzyl-β-L-idopyranuronate of general formula 24 (where $Z^3$=Ac, $NR^{12}$=$N_3$, $R^9$=Bn, $R^{10}$=PMB, $R^{11}$=Bn, X=OMe, $R^3$=Bn, $R^5$=Ac) was prepared as follows.

To 2.49 g (3.83 mmol) of the trichloroacetimidate donor 26 (where $Z^4$=OTCA, $NR^{12}$=$N_3$, $R^9$=Bn, $R^{10}$=PMB, $R^{11}$=Ac) and 1.39 g (3.64 mmol) of the iduronic ester acceptor 12′″ in separate flasks was added dry toluene and evaporated twice. The residues were dried for 2 h and placed under Argon, then DCM (15 mL) was added to the acceptor and dry DCM (7 mL) to the donor. The acceptor solution was cooled to −30° C. then 7 μL (0.039 mmol) of TMSOTf was added and the donor was added dropwise over 30 min and the mixture was kept at this temperature for another 10 min, then quenched with two drops of $NEt_3$. The solvent was removed and column chromatography yielded 2.08 g (66%) of the disaccharide.

The disaccharide produced above can then be used to prepare the corresponding glycosyl donor/acceptor compounds using similar chemistry to that set out above in respect of the first precursor.

Alternative Method for Producing an L-Iduronate Containing Polysaccharide

An alternative method for the production of an L-iduronate containing polysaccharide (2-Azido-3-O-benzyl-4-O-p-methoxybenzyl-6-O-acetyl-2-deoxy-α-D-glucopyranosyl-(1→4)-methyl 2-O-acetyl-3-O-benzyl-β-L-idopyranosyluronate-(1→4)-2-azido-3-O-benzyl-6-O-acetyl-2-deoxy-α-D-glucopyranosyl-(1→4)-methyl 1,2-di-O-acetyl-3-O-benzyl-β-L-idopyranouronate) is now described (structure shown below). Similar basic coupling chemistry may be used to produce polysaccharide 34′.

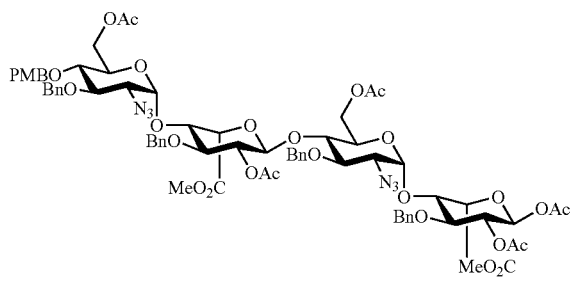

To 458 mg (0.496 mmol) of a donor disaccharide of general formula 24 (where $Z^3$=OTCA, $NR^{12}$=$N_3$, $R^9$=Bn, $R^{10}$=PMB, $R^{11}$=Ac, X=OMe, $R^3$=Bn, $R^5$=Ac) and 268 mg (0.382 mmol) of an acceptor disaccharide of general formula 24 (where $Z^3$=Ac, $NR^{12}$=$N_3$, $R^9$=Bn, $R^{10}$=H, $R^{11}$=Ac, X=OMe, $R^3$=Bn, $R^5$=Ac) was added dry toluene and evaporated twice. The residue was dried for 2 h and then placed under Argon, dry DCM (5 mL) was added and the solution was cooled to −35° C. Then TMSOTf (5 μL, 0.028 mmol) was added dropwise and the mixture was kept at −35° C. to −20° C. for 2 h. and then quenched with two drops of $NEt_3$. The solvent was evaporated and column chromatography yielded 253 mg (45%) of the tetrasacharide.

Alternative Method for Producing an L-Iduronate Containing Polysaccharide

An alternative method for the production of an L-iduronate containing polysaccharide is now described. Similar basic coupling chemistry may be used to produce polysaccharide 34.

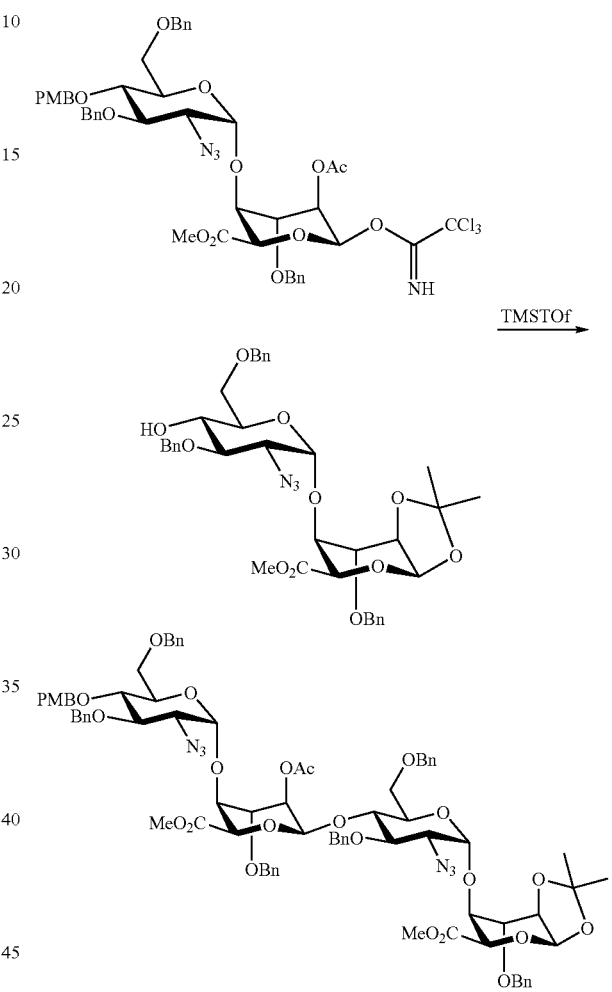

A mixture of a donor disaccharide TCA derivative (16 mg, 0.0164 mmol, 1.3 eq), an acceptor disaccharide (8.9 mg, 0.0127 mmol), molecular sieves (20 mg) and DCM (0.2 mL) was stirred for 10 min. at r.t. then cooled to −25° C. and stirred for another 10 min. TMSTOf (32.8 uL from 0.1M in DCM, 0.00328 mmol, 0.2 eq) was then added. The mixture was allowed to warm to r.t. over 1.5 h, quenched with $Et_3N$ and evaporated and a tetrasacharide isolated by column chromatography using Hex:EtOAc.

COMPARATIVE EXAMPLES

Comparative Example 1

The reaction shown below was repeated in the presence of different salts and different molar equivalent amounts of magnesium chloride to investigate their effect on the ratio of products 5 and 6 obtained.

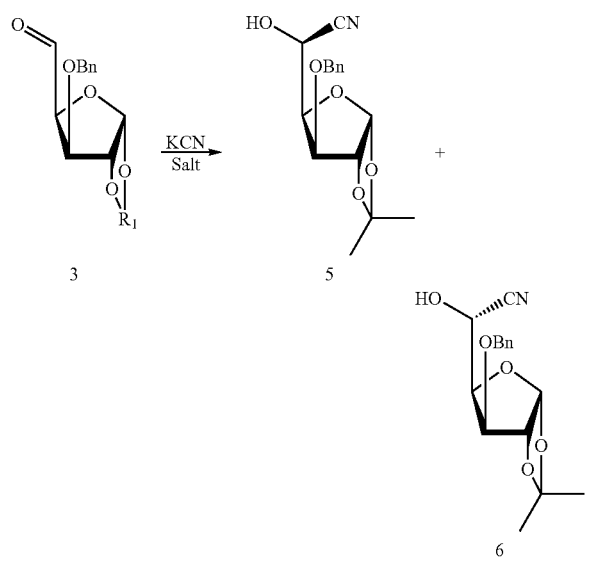

Each reaction was carried out using 1.1. molar equivalents of potassium cyanide and was effected over a time period of 48 hours. All reactions were carried out at room temperature in an ethanolic solvent (1:1, ethanol:water). The molar equivalent amounts of potassium cyanide and the salts used were calculated with reference to the amount of aldehyde 3

Table 1 below presents the stereochemical product ratio (5:6) and total product yield obtained for the various reactions of potassium cyanide with the aldehyde 3.

TABLE 1

| Salt | Molar Equiv. Amount of Salt | Total Product Yield | Product Ratio 5:6 |
|---|---|---|---|
| $MgCl_2$ | 0.1 | 60% | 1:1 |
| $MgCl_2$ | 0.55 | 80% | 10:1 |
| $CaCl_2$ | 1.1 | 59% | 4:5 |
| $MgSO_4$ | 1.1 | 76% | 11:1 |
| $MgBr_2$ | 1.1 | 77% | 10:1 |

Comparative Example 2

The reaction of aldehyde 3 with 1.1 molar equivalents of potassium cyanide was repeated employing reaction times of 3 and 5 days. Both reactions were carried out in the presence of 1.1 molar equivalents of magnesium chloride at room temperature (rt) in an ethanolic solvent (1:1, ethanol:water).

The reaction of aldehyde 3 with potassium cyanide was repeated using different amounts of magnesium chloride, and employing different solvents, temperatures and reaction times to investigate how each of these parameters affected the product ratio obtained.

Table 2 below presents the stereochemical product ratio (5:6) and total product yield obtained for the above described reactions of aldehyde 3 with potassium cyanide.

TABLE 2

| $MgCl_2$ (mol. eq.) | KCN (mol. eq.) | Solvent | Time | Temp. | Total Yield % | Product ratio 5:6 |
|---|---|---|---|---|---|---|
| 1.1 | 1.1 | EtOH/$H_2O$ 1:1 | 3 days | rt | 64 | 3:1 |
| 1.1 | 1.1 | EtOH/$H_2O$ 1:1 | 5 days | rt | 93 | 20:1 |

TABLE 2-continued

| $MgCl_2$ (mol. eq.) | KCN (mol. eq.) | Solvent | Time | Temp. | Total Yield % | Product ratio 5:6 |
|---|---|---|---|---|---|---|
| 1.1 | 1.1 | EtOH/$H_2O$ 2:1 | 16 hrs | rt | 76 | 2:1 |
| 5 | 1.2 | EtOH/$H_2O$ 3:1 | 90 min | 0° C. | 8 | 3:2 |
| 1.1 | 2 + CuCN (1.1 eq.) | THF | 16 hrs | rt | 86 | 1:1 |
| 1.1 | 1.1 | THF/$H_2O$ 2:1 | 15 min | 0° C. | 78 | 2:3 |

Comparative Example 3

The reaction of aldehyde 3 with 1.1 molar equivalents of potassium cyanide was repeated employing different reaction times and then using different concentrations of compound 3 at a constant reaction time of 16 hours. All reactions were carried out in the presence of 1.1 molar equivalents of magnesium chloride at room temperature (rt) in an ethanolic solvent (1:1, ethanol:water).

TABLE 3

| Cmpd 3 Conc. M | Time | Total Yield % | Product Ratio 5:6 | Diastereoisomeric Excess % |
|---|---|---|---|---|
| 0.3 | 20 min. | 97 | 6:5 | 9 |
| 0.3 | 1 hr | 94 | 2:1 | 28 |
| 0.3 | 2 hr | 94 | 39:7 | 69 |
| 0.3 | 4 hr | 96 | 20:3 | 74 |
| 0.3 | 16 hr | 94 | 10:1 | 82 |
| 0.3 | 48 hr | 94 | 15:1 | 87 |
| 0.3 | 5 days | 93 | 20:1 | 90 |
| 0.55 | 16 hr | 93 | 11:1 | 83 |
| 0.19 | 16 hr | 91 | 21:3 | 75 |
| 0.06 | 16 hr | 96 | 2:1 | 36 |

REFERENCES

1. Rochepeau-Jobron, L.; Jacquinet, J-C. *Carbohydr. Res.* 1997, 303, 395-406.
2. Hinou, H.; Kuorsawa, H.; Matsuokak, K.; et al *Tetrahedron Lett.* 1999, 40, 1501-1504.
3. Schell, P.; Orgueira, H. A.; Roehrig, S. et al: Synthesis and transformation of D-glucoronic and L-iduronic acid glycals. *Tetrahedron Lett.* 2001, 42, 3811-3814.
4. Orgueira, H. A.; Bartolozzi, A.; Schell, P. et al *Chem. Eur. J.* 2003, 9, 140-169.
5. Ke, W.; Whitfield, D. M.; Gill, M.; et al *Tetrahedron Lett.* 2003, 44, 7767-7770.
6. Ojeda, R.; de Paz, J L.; Martín-Lomas, M.; et al: A New Route to L-Iduronate Building-blocks for the Synthesis of Heparin-like Oligosaccharides. Syn. Lett. 1999, 1316-1318.
7. Jacquinet, J-C.; Petitoi, M.; Duchaussoy, P.; et al *Carbohydr. Res.* 1984, 130, 221-241.
8. Lohman, G. J. S.; Hunt, D. K.; Hogermeier, J. A.; et al: *J. Org. Chem.*, 2003, 68, 7559-7561.
9. Gavard, O.; Hersant, Y. I.; Alais, J.; et al *Eur. J. Org. Chem.* 2003, 3603-3620.
10. (a) *J. Carbohydr. Chem.* 1987, 6, 259-272. (b) Wolfrom, M. L.; Thomas, G. H. S. *Methods in Carbohydr. Chem.*, Year/Vol, 32-35.

11. Methods in Carbohydrate Chemistry. Volume II, p. 320-321.
12. Vogel's Textbook of Practical Organic Chemistry. 5th Edition. P. 656.
13. D. Bonaffé et al., *Eur. J. Org. Chem.* 2003, 3603-3620.

The invention claimed is:

1. A process for converting α-D-glucose 4 to 1,2-O-isopropylidene-α-L-idofuranonitrile 5' via 1,2-O-isopropylidene-α-D-xylo-dialdose 3'

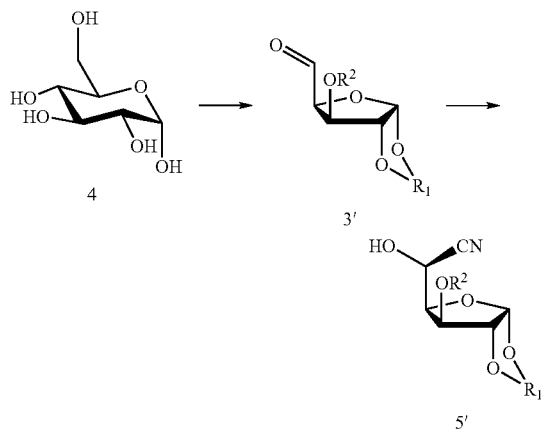

where $R^1$ is an alkylene group and $R^2$ is a protecting group, wherein the conversion of compound 3' to compound 5' is effected by reacting compound 3' with cyanide ions in the presence of magnesium ions.

2. A process according to claim 1, wherein the molar ratio of magnesium ions to cyanide ions is in the range 0.5 to 2.

3. A process according to claim 1, wherein the cyanide ions are provided in an amount of at least approximately 1 equivalent by mole based on the amount of compound 3'.

4. A process according to claim 1, wherein the source of the cyanide ions is selected from the group consisting of potassium cyanide, sodium cyanide, hydrogen cyanide and lithium cyanide.

5. A process according to claim 1, wherein the source of the magnesium ions is selected from the group consisting of a magnesium halide and magnesium sulphate.

6. A process according to claim 5, wherein the magnesium halide is magnesium chloride.

7. A process according to claim 1, wherein the reaction to convert compound 3' to compound 5' is conducted at a temperature in the range 0° C. to 40° C.

8. A process according to claim 1, wherein the reaction to convert compound 3' to compound 5' is carried out at around room temperature.

9. A process according to claim 1, wherein compound 3' is converted to, compound 5' employing a reaction time of 1 hour to 10 days.

10. A process according to claim 1, wherein compound 3' is converted to compound 5' employing a reaction time of 2 to 5 days.

11. A process according to claim 1, wherein the reaction of compound 3' with cyanide ions is carried out in an alcoholic solvent.

12. A process according to claim 11, wherein the alcohol present in the solvent is an alkanol.

13. A process according to claim 11, wherein the solvent is an aqueous alcoholic solvent.

14. A process according to claim 13, wherein the ratio of alcohol to water is preferably in the range 3:1 to 1:3.

15. A process according to claim 1, wherein the reaction of compound 3' with cyanide ions in the presence of magnesium ions generates a product mixture comprising compound 5' and compound 6'

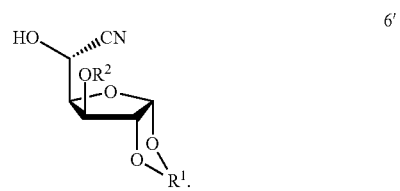

16. A process according to claim 15, wherein the conversion of compound 3' to compound 5' is carried out under stereoselective conditions to provide a product ratio of 5':6' of greater than 2:1.

17. A process according to claim 15, wherein the conversion of compound 3' to compound 5' is carried out under stereoselective conditions to provide a product ratio of 5':6' of greater than 10:1.

18. A process according to claim 15, wherein compound 5' is isolated from the product mixture by crystallisation.

19. A process according to claim 18, wherein compound 5' is crystallised by forming a solution of the product mixture in an aprotic organic solvent and then adding a non-polar solvent to said solution.

20. A process according to claim 19, wherein the aprotic organic solvent is selected from the group consisting of diethylether and ethylacetate.

21. A process according to claim 19, wherein the non-polar solvent is hexane.

22. A process according to claim 15, wherein the process further comprises adding cyanide ions in the presence of magnesium ions to residual non-crystallised product mixture remaining after crystallisation of compound 5' from the product mixture to provide a further product mixture containing additional compound 5', and isolating a further amount of compound 5' from said further product mixture.

23. A process according to claim 1, wherein $R^1$ provides at least one carbon atom between the C1 and C2 oxygen atoms.

24. A process according to claim 1, wherein $R^1$ is a methylene group or an isopropyl group.

25. A process according to claim 1, wherein $R^2$ is a benzyl group.

26. A process for converting 1,2-O-isopropylidene-α-L-idofuranonitrile 5' to a compound having formula 7

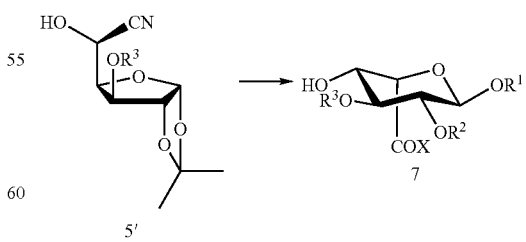

where $R^1$, $R^2$ and $R^3$ are the same or different protecting groups and X is selected from the group consisting of —NH$_2$, —OH and —OR, wherein the process comprises converting the C5 cyano group of compound 5' to the —COX group of compound 7, deprotecting the C1 and C2 oxygen atoms and then adding protecting groups R¹ and R² to the C1 and C2 oxygen atoms.

27. A process according to claim 26, wherein R¹, R² and R³ are each separately selected from the group consisting of a substituted or unsubstituted acyl protecting group, substituted or unsubstituted carbocyclic protecting group and substituted or unsubstituted heterocyclic protecting group.

28. A process according to claim 26, wherein R¹, R² and R³ are each separately selected from the group consisting of an acetyl group, a benzyl group and a tetrahydropyranyl group.

29. A process according to claim 26, wherein compound 7 is 1,2-di-O-acetyl-3-O-benzyl-β-L-idopyranuronamide 8

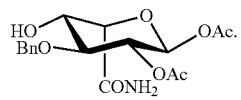

8

30. A process according to claim 29, wherein addition of acetyl groups to the C1 and C2 oxygen atoms is effected by the addition of acetic anhydride or an acetyl halide.

31. A process according to claim 29, wherein addition of acetyl groups to the C1 and C2 oxygen atoms is carried out in the presence of dimethylaminopyridine.

32. A process according to claim 29, wherein addition of acetyl groups to the C1 and C2 oxygen atoms is carried out over a period of 4 to 8 hours.

33. A process according to claim 29, wherein addition of acetyl groups to the C1 and C2 oxygen atoms is carried out over a period of approximately 6 hours.

34. A process according to claim 29, wherein addition of acetyl groups to the C1 and C2 oxygen atoms is carried out at a temperature in the range 10 to 30° C.

35. A process according to claim 29, wherein addition of acetyl groups to the C1 and C2 oxygen atoms is carried out at room temperature.

36. A process according to claim 29, wherein the C5 cyano group is hydrolysed to an amide group in the presence of an acid catalyst.

37. A process according to claim 29, wherein the process further comprises crystallising compound 8 by forming a solution of compound 8 in an aprotic organic solvent and then adding a non-polar solvent to said solution.

38. A process according to claim 37, wherein the aprotic organic solvent is selected from the group consisting of diethylether and ethylacetate.

39. A process according to claim 37, wherein the non-polar solvent is hexane.

40. A process according to claim 26, wherein the C1 and C2 oxygen atoms are deprotected by the addition of aqueous acid.

41. A process according to claim 40, wherein the aqueous acid is aqueous hydrochloric acid.

42. A process according to claim 26, wherein compound 7 is methyl 3-O-benzyl-1,2-O-isopropylidene-β-L-idopyranosyluronate 12

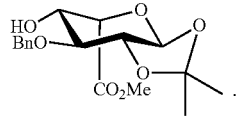

12

43. A process according to claim 42, wherein compound 12 is formed by converting the amide group of 3-O-benzyl-1,2-O-isopropylidene-□-L-idopyranuronamide 15 to an ester group

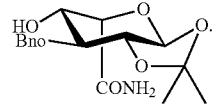

15

44. A process according to claim 43, wherein the conversion of the amide group of compound 15 to an ester group is effected by the addition of dimethylformamide dimethylacetal.

45. A process according to claim 43, wherein compound 15 is formed by converting the cyano group of 3-O-benzyl-1,2-O-isopropylidene-β-L-idopyranonitrile 14 to an amide group

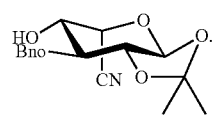

14

46. A process according to claim 45, wherein the conversion of the cyano group of compound 14 to an amide group is effected by the addition of an oxidising agent.

47. A process according to claim 46, wherein the oxidising agent is hydrogen peroxide.

48. A process according to claim 47, wherein the hydrogen peroxide is added in the presence of potassium carbonate.

49. A process according to claim 45, wherein compound 14 is formed by converting the C1 and C2 hydroxyl groups of 3-O-Benzyl-L-idopyranonitrile 13 to form part of a cyclic acetal group

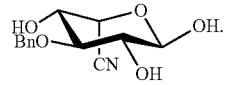

13

50. A process according to claim 49, wherein the cyclic acetal group is an isopropylidene group.

51. A process according to claim 49, wherein the conversion of compound 13 to compound 14 is effected by the addition of 2-methoxypropene in the presence of camphorsulfonic acid followed by replacement of the resulting C4-2-methoxy-isopropyl group with a hydroxyl group by adding p-toluenesulfonic acid mono hydrate.

52. A process according to claim 49, wherein compound 13 is formed by acid catalysed deprotection of the C1 and C2 oxygen atoms of compound 5'.

53. A process according to claim 52, wherein the acid is trifluoroacetic acid.

54. A compound having the formula 7'

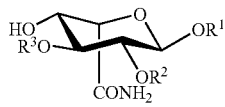

where $R^1$, $R^2$ and $R^3$ are the same or different protecting groups.

55. A compound according to claim 54, wherein $R^1$, $R^2$ and $R^3$ are each separately selected from the group consisting of a substituted or unsubstituted acyl protecting group, substituted or unsubstituted carbocyclic protecting group and substituted or unsubstituted heterocyclic protecting group.

56. A compound according to claim 54, wherein $R^1$, $R^2$ and $R^3$ are each separately selected from the group consisting of an acetyl group, a benzyl group and a tetrahydropyranyl group.

57. A compound 1,2-di-O-acetyl-3-O-benzyl-β-L-idopyranuronamide 8

58. A compound 3-O-benzyl-1,2-O-isopropylidene-β-L-idopyranonitrile 14

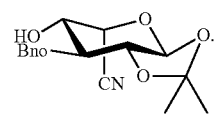

59. A compound 3-O-benzyl-1,2-O-isopropylidene-β-L-idopyranuronamide 15

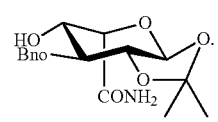

60. A process for producing compound 12' from compound 5'

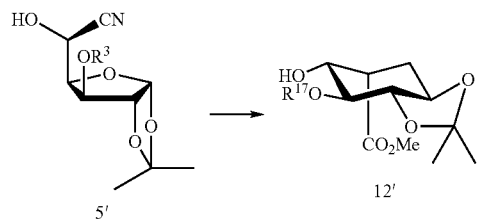

where $R^3$ and $R^{17}$ are the same of different protecting groups and the process comprises deprotecting the C1 and C2 oxygen atoms of compound 5', reprotecting the C1 and C2 oxygen atoms, and converting the C5 cyano group to an ester group.

61. A process for converting 1,2-O-isopropylidene-α-L-idofuranonitrile 5' to a compound having formula 11'

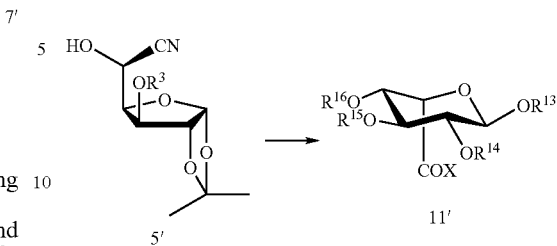

where $R^3$, $R^{13}$, $R^{14}$, $R^{15}$ and $R^{16}$ are the same or different protecting groups and X is selected from the group consisting of —$NH_2$, —OH and —OR, wherein the process comprises converting the C5 cyano group of compound 5' to the —COX group of compound 11', deprotecting the C1 and C2 oxygen atoms and then adding protecting groups $R^{13}$, $R^{14}$ and $R^{16}$ to the C1, C2 and C4 oxygen atoms respectively.

62. A process according to claim 61, wherein $R^3$, $R^{13}$, $R^{14}$, $R^{15}$ and $R^{16}$ are each separately selected from the group consisting of a substituted or unsubstituted acyl protecting group, substituted or unsubstituted carbocyclic protecting group and substituted or unsubstituted heterocyclic protecting group.

63. A process according to claim 61, wherein $R^3$, $R^{13}$, $R^{14}$, $R^{15}$ and $R^{16}$ are each separately selected from the group consisting of an acetyl group, a benzyl group and a tetrahydropyranyl group.

64. A process according to claim 61, wherein compound 11' is 1,2,4-tri-O-acetyl-3-O-benzyl-β-L-idopyranuronamide 11

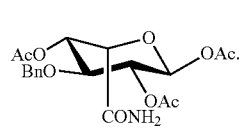

65. A process according to claim 64, wherein addition of acetyl groups to the C1, C2 and C4 oxygen atoms is effected by the addition of acetic anhydride or an acetyl halide.

66. A process according to claim 64, wherein addition of acetyl groups to the C1, C2 and C4 oxygen atoms is carried out in the presence of pyridine.

67. A process according to claim 64, wherein addition of acetyl groups to the C1, C2 and C4 oxygen atoms is carried out over a period of 1 to 2 hours.

68. A process according to claim 64, wherein the addition of acetyl groups to the C1, C2 and C4 oxygen atoms is carried out over a period of approximately 1.5 hours.

69. A process according to claim 64, wherein the addition of acetyl groups to the C1, C2 and C4 oxygen atoms is carried out at a temperature in the range 10 to 30° C.

70. A process according to claim 64, wherein the addition of acetyl groups to the C1, C2 and C4 oxygen atoms is carried out at room temperature.

71. A process according to claim 64, wherein the C5 cyano group is hydrolysed to an amide group in the presence of an acid catalyst.

72. A process according to claim 64, wherein the C1 and C2 oxygen atoms are deprotected by the addition of aqueous acid.

73. A process according to claim 72, wherein the aqueous acid is aqueous hydrochloric acid.

74. A compound having the formula 11″

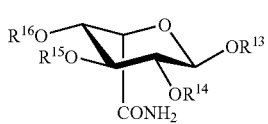

where $R^{13}$, $R^{14}$, $R^{15}$ and $R^{16}$ are the same or different protecting groups, and where at least one of $R^{13}$, $R^{14}$, $R^{15}$ and $R^{16}$ is not acetyl.

75. A compound according to claim 74, wherein $R^{13}$, $R^{14}$, $R^{15}$ and $R^{16}$ are each separately selected from the group consisting of a substituted- or unsubstituted acyl protecting group, substituted or unsubstituted carbocyclic protecting group and substituted or unsubstituted heterocyclic protecting group.

76. A compound according to claim 74, wherein $R^{13}$, $R^{14}$, $R^{15}$ and $R^{16}$ are each separately selected from the group consisting of an acetyl group, a benzyl group and a tetrahydropyranyl group.

77. A compound 1,2,4-tri-O-acetyl-3-O-benzyl-β-L-idopyranuronamide 11

78. A process for converting a compound of formula 8 to a compound of formula 12‴

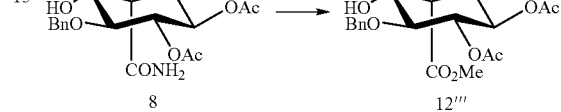

wherein the process comprises reacting compound 8 with a nitrite compound and addition of DMF/DMA.

79. A process for converting compound 8 to compound 22″″

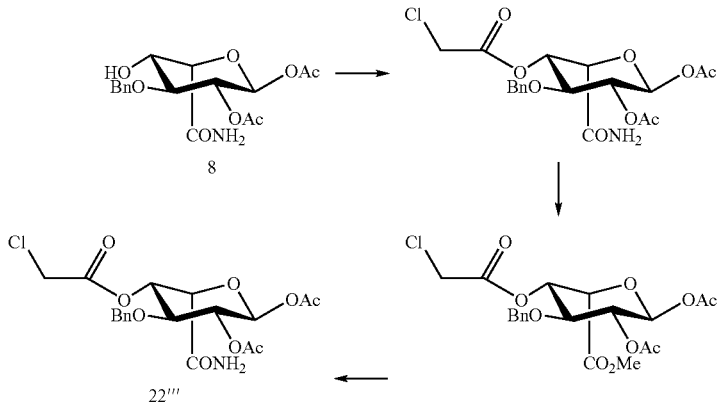

wherein conversion of the C5 amide group to a C5 ester group is effected by the addition of a nitrite compound and DMF/DMA.

80. A process for the conversion of compound 5′ to compound 12A

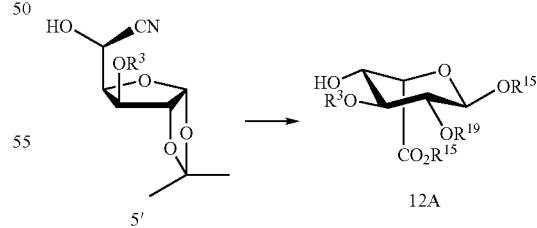

where $R^3$ is a protecting group, $R^{18}$ is a branched or unbranched, substituted or unsubstituted alkyl group, and $R^{19}$ is a protecting group, wherein the process comprises the addition of an alcohol $R^{18}OH$ in the presence of an acid catalyst.

* * * * *

UNITED STATES PATENT AND TRADEMARK OFFICE
CERTIFICATE OF CORRECTION

PATENT NO. : 7,919,599 B2
APPLICATION NO. : 11/921523
DATED : April 5, 2011
INVENTOR(S) : Gordon Jayson, John M. Gardiner and Steen Uldall Hansen It is certified that error appears in the above-identified patent and that said Letters Patent is hereby corrected as shown below:

In the Specification
Column 3, line 63, "are" should read --is--.
Column 4, line 4, "oα-L-" should read --α-L- --.
Column 13, line 8, after "such as" insert --a--.
Column 13, line 12, delete "a", both occurrences.
Column 17, line 59, "two step" should read --two-step--.
Column 17, line 60, "four step" should read --four-step--.
Column 17, line 61, "two step" should read --two-step--.
Column 17, line 65, "two step" should read --two-step--.
Column 19, line 61, "Where" should read --where--.
Column 25, line 67, before "thiophenyl" insert --the--.
Column 29, line 29, "Where" should read --where--.
Column 31, line 29, "Where" should read --where--.
Column 42, line 67, "hour" should read --hours--.
In the Claims
Column 49, line 56, after "to" delete "," .
Column 52, line 11, "□" should read --β--.
Column 53, line 63, "of" should read --or--.
Column 56, claim 79, delete the illustrated formula and replace it with the following

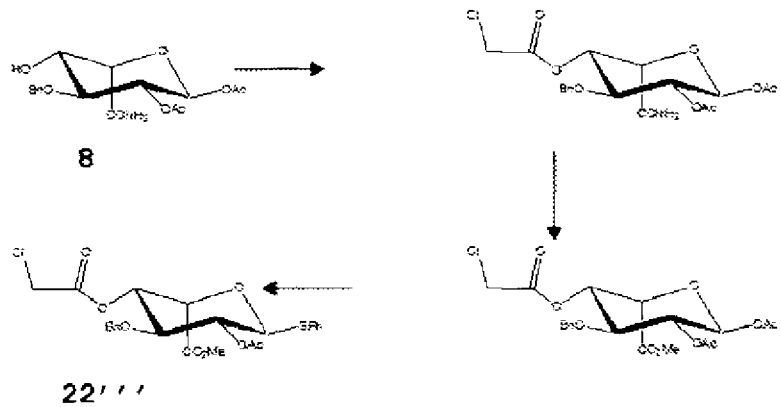

Signed and Sealed this
Twenty-seventh Day of August, 2013

Teresa Stanek Rea
*Acting Director of the United States Patent and Trademark Office*